United States Patent
Masuda et al.

(10) Patent No.: US 12,161,875 B2
(45) Date of Patent: *Dec. 10, 2024

(54) WEARABLE MEDICAL DEVICE FOR CONTINUOUS HEART MONITORING WITH INTERMITTENT ADDITIONAL SIGNAL DATA PROVIDED VIA ONE OR MORE TOUCH-SENSITIVE ELECTRODES

(71) Applicant: ZOLL Medical Corporation, Chelmsford, MA (US)

(72) Inventors: Tsuyoshi Masuda, Pittsburgh, PA (US); Gary A. Freeman, Waltham, MA (US); Kent Volosin, Mars, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/234,686

(22) Filed: Aug. 16, 2023

(65) Prior Publication Data

US 2023/0390567 A1 Dec. 7, 2023

Related U.S. Application Data

(63) Continuation of application No. 15/923,812, filed on Mar. 16, 2018, now Pat. No. 11,786,744.

(51) Int. Cl.
*A61B 5/00* (2006.01)
*A61B 5/024* (2006.01)
(Continued)

(52) U.S. Cl.
CPC .......... *A61N 1/3904* (2017.08); *A61B 5/0006* (2013.01); *A61B 5/02438* (2013.01);
(Continued)

(58) Field of Classification Search
CPC .... A61N 1/3904; A61N 1/046; A61N 1/3987; A61N 1/3993; A61B 5/259; A61B 5/364;
(Continued)

(56) References Cited

U.S. PATENT DOCUMENTS

| | | |
|---|---|---|
| 6,253,099 B1 | 6/2001 | Oskin et al. |
| 8,428,682 B1 | 4/2013 | Rood et al. |

(Continued)

FOREIGN PATENT DOCUMENTS

WO 2016161152 10/2016

OTHER PUBLICATIONS

Burch, "The History of Vectorcardiography," Medical History, Supplement No. 5:103-131 (1985). (Submitted in related U.S. Appl. No. 15/923,812.).

(Continued)

*Primary Examiner* — Adam Z Minchella
(74) *Attorney, Agent, or Firm* — Gardella Grace P.A.

(57) ABSTRACT

A wearable medical device is provided for monitoring a cardiac condition of a patient, where the device is releasably mounted to the patient's chest and includes at least two skin-facing electrodes forming a first one or more ECG leads for ongoing monitoring of heart functioning and at least one touch electrode for intermittently obtaining additional circuit vectors for deriving additional metrics regarding the functioning of the patient's heart. Each touch electrode is configured to form an additional lead/vector that is a larger vector and/or separated by at least 15° from a corresponding first lead/vector formed from the first one or more ECG leads in a vector cardiogram representation of the first one or more ECG leads and the additional lead/vector.

20 Claims, 16 Drawing Sheets

(51) Int. Cl.

| | |
|---|---|
| *A61B 5/0245* | (2006.01) |
| *A61B 5/24* | (2021.01) |
| *A61B 5/259* | (2021.01) |
| *A61B 5/282* | (2021.01) |
| *A61B 5/333* | (2021.01) |
| *A61B 5/341* | (2021.01) |
| *A61B 5/364* | (2021.01) |
| *A61N 1/04* | (2006.01) |
| *A61N 1/39* | (2006.01) |

(52) U.S. Cl.
CPC ............ *A61B 5/0245* (2013.01); *A61B 5/259* (2021.01); *A61B 5/282* (2021.01); *A61B 5/333* (2021.01); *A61B 5/341* (2021.01); *A61B 5/364* (2021.01); *A61N 1/046* (2013.01); *A61N 1/3987* (2013.01); *A61N 1/3993* (2013.01); *A61B 2562/0204* (2013.01); *A61B 2562/0209* (2013.01); *A61B 2562/04* (2013.01); *A61B 2562/221* (2013.01)

(58) Field of Classification Search
CPC ......... A61B 5/282; A61B 5/333; A61B 5/341; A61B 5/0006; A61B 5/02438; A61B 5/0245; A61B 2562/0204; A61B 2562/0209; A61B 2562/04; A61B 2562/221

See application file for complete search history.

(56) References Cited

U.S. PATENT DOCUMENTS

| | | | |
|---|---|---|---|
| 9,545,209 B2 | 1/2017 | Weng et al. | |
| 9,579,514 B2 | 2/2017 | Freeman et al. | |
| 9,737,701 B2 | 8/2017 | Dupelle et al. | |
| 9,839,363 B2 | 12/2017 | Albert | |
| 9,867,976 B2 | 1/2018 | Freeman | |
| 2006/0224072 A1 | 10/2006 | Shennib | |
| 2006/0229521 A1 | 10/2006 | Barr | |
| 2007/0149888 A1 | 6/2007 | Kohls et al. | |
| 2010/0076331 A1 | 3/2010 | Chan et al. | |
| 2010/0324384 A1 | 12/2010 | Moon et al. | |
| 2011/0288605 A1 | 11/2011 | Kaib et al. | |
| 2012/0059270 A1* | 3/2012 | Grunwald | A61B 5/352 600/509 |
| 2014/0058280 A1 | 2/2014 | Chefles et al. | |
| 2014/0073979 A1 | 3/2014 | Inciardi et al. | |
| 2014/0114142 A1 | 4/2014 | Shaoulian | |
| 2015/0087921 A1 | 3/2015 | Felix et al. | |
| 2015/0297134 A1 | 10/2015 | Albert et al. | |
| 2016/0089081 A1* | 3/2016 | Morris | A61B 5/681 600/382 |
| 2016/0135706 A1 | 5/2016 | Sullivan et al. | |
| 2016/0296132 A1* | 10/2016 | Bojovic | G16H 40/63 |
| 2017/0000415 A1 | 1/2017 | Lapetina et al. | |
| 2017/0258349 A1* | 9/2017 | Watanabe | A61B 5/0245 |
| 2019/0159676 A1* | 5/2019 | Murphy | A61B 5/0022 |
| 2019/0282821 A1 | 9/2019 | Masuda et al. | |

OTHER PUBLICATIONS

Shu, et al. "Bared Microtip Arrays for ECG Measurement," International Journal of Automation and Smart Technology, vol. 6, No. 3, pp. 177-180 (2016). (Submitted in related U.S. Appl. No. 15/923,812.).

Neuman, Michael R., "Biopotential Amplifiers," pp. 1-51. (Submitted in related U.S. Appl. No. 15/923,812.).

de Groot, et al. "Electrical Measurements on the Human Body," pp. 1-42 (2008). (Submitted in related U.S. Appl. No. 15/923,812.).

Kennedy, et al. "Detecting the Elusive P-Wave: A New ECG Lead to Improve the Recording of Atrial Activity," IEEE Transactions on Biomedical Engineering, vol. 63: No. 2, pp. 243-249 (2016). (Submitted in related U.S. Appl. No. 15/923,812.).

Nedios, et al. "Precordial electrode placement for optimal ECG monitoring: Implications for ambulatory monitor devices and event recorders," Journal of Electrocardiology 45:669-676 (2014). (Submitted in related U.S. Appl. No. 15/923,812.).

LifeVest TruVector Arrhythmia Detection Algorithm, pp. 1-8, <https:lifevest.mymarketingbench.com/images/1/21-90020000/20C0010.pdf> (Submitted in related U.S. Appl. No. 15/923,812.).

Kyma Medical Technologies Ltd. "Non-Invasive Monitoring System," uCor V3.0.0—User Guide, pp. 1-25 (2014). (Submitted in related U.S. Appl. No. 15/923,812.).

Kyma Medical Technologies Ltd. u-Cor Patient Leaflet, pp. 1-2 (2014). (Submitted in related U.S. Appl. No. 15/923,812.).

AliveCor, Inc. Bridging the Gap Between Wearables and Healthcare, pp. 1-23 <https://www.alivecor.com/technology/> (Submitted in related U.S. Appl. No. 15/923,812.).

AliveCor, Inc. User Manual for Kardia by AliveCor, 08LB12 Revision 3, pp. 1-33, <https://www.alivecor.com/previous-labeling/kardia/08LB12.3.pdf> (Submitted in related U.S. Appl. No. 15/923,812.).

EkoDuo, User Manual, Model E5, pp. 1-21, <https://cache.ekodevices.com/wp-content/uploads/2017/06/LBL-009-Eko-DUO-User-Manual-Rev-B.pdf> (Submitted in related U.S. Appl. No. 15/923,812.).

ApoDx Technology, Inc. DxPatch Electrocardiogramo Recorder User Guide—Model No. 8ZP7, pp. 1-25, <https://ficcid.io/2AF6P8ZP7/User-Manual/Users-Manual-3062749.pdf> (Submitted in related U.S. Appl. No. 15/923,812.).

Non-Final Office Action mailed in related U.S. Appl. No. 15/923,812 on Oct. 18, 2021, 28 pages.

Final Office Action mailed in related U.S. Appl. No. 15/923,812 on Mar. 3, 2022, 29 pages.

Non-Final Office Action mailed in related U.S. Appl. No. 15/923,812 on Jul. 12, 2022, 31 pages.

Final Office Action mailed in related U.S. Appl. No. 15/923,812 on Jan. 24, 2023, 29 pages.

Notice of Allowance mailed in related U.S. Appl. No. 15/923,812 on May 22, 2023, 9 pages.

* cited by examiner

WEARABLE MEDICAL DEVICE FOR CONTINUOUS HEART MONITORING WITH INTERMITTENT ADDITIONAL SIGNAL DATA PROVIDED VIA ONE OR MORE TOUCH-SENSITIVE ELECTRODES

RELATED APPLICATIONS

This application is a continuation of and claims priority to U.S. patent application Ser. No. 15/923,812, entitled "Wearable Medical Device for Continuous Heart Monitoring with Intermittent Additional Signal Data Provided Via One or More Touch Sensitive Electrodes," filed Mar. 16, 2018, which is incorporated by reference herein in its entirety.

BACKGROUND

The present disclosure is directed to wearable medical devices for ongoing monitoring of heart functioning. There are a wide variety of electronic and mechanical devices for monitoring and treating patients' medical conditions. In some examples, depending on the underlying medical condition being monitored or treated, medical devices such as cardiac monitors or defibrillators may be surgically implanted or externally connected to the patient. In some cases, physicians may use medical devices alone or in combination with drug therapies to treat conditions such as cardiac arrhythmias.

One of the most deadly cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity) result in the heart providing insufficient levels of blood flow to the brain and other vital organs for the support of life.

Cardiac arrest and other cardiac health ailments are a major cause of death worldwide. The sooner associated symptoms of these conditions are detected, the better the patient's healthcare provider's ability to intervene. Non-invasive cardiac monitoring devices in an out-patient setting aim to monitor cardiac function, detect irregularities, and provide continuous, but limited, cardiac data to the healthcare provider. Non-invasive cardiac monitoring can be done in a variety of ways including electrically (electrocardiogram (ECG)), optically (pulse Ox), acoustically (heart vibrations) among other methods.

SUMMARY

In one aspect, embodiments of a wearable medical device for monitoring a cardiac condition of a patient, includes a substrate having a first side and a second side opposite the first side; at least two ECG electrodes disposed on the first side of the substrate and configured to be in continuous contact with skin of the patient; one or more touch electrodes disposed on the second side of the substrate and configured to be contacted with one or more portions of one or more arms of the patient; ECG circuitry in communication with the at least two ECG electrodes and the one or more touch electrodes; a memory in communication with the ECG circuitry; and at least one processor in communication with the memory and the ECG circuitry, the at least one processor configured to receive a first set of electrical signals from the at least two ECG electrodes in continuous contact with the skin of the patient, generate first one or more ECG leads from the received first set of electrical signals, receive a second set of electrical signals from a predetermined combination of the at least two ECG electrodes disposed on the first side of the substrate and the one or more touch electrodes disposed on the second side of the substrate when the one or more touch electrode is contacted with one or more portions of one or more arms of the patient, generate second one or more ECG leads from the received second set of electrical signals, and store ECG lead data corresponding the first one or more ECG leads and the second one or more ECG leads in the memory.

In some implementations, the one or more touch electrodes includes a single touch electrode that is configured to be contacted with a finger of the right or left arm of the patient.

In some implementations, the one or more touch electrodes includes two touch electrodes that are configured to be contacted with a left finger of the left arm of the patient and a right finger of the right arm of the patient respectively.

In some implementations, the first one or more ECG leads are each separated by at least from a corresponding second one or more ECG leads in a vector cardiogram representation of the first one or more ECG leads and the second one or more ECG leads.

In some implementations, the first one or more ECG leads are each separated by at least from a corresponding second one or more ECG leads includes the first one or more ECG leads being each separated by between around at least one of: 15° to around 90° from the corresponding second one or more ECG leads, 15° to around 135° from the corresponding second one or more ECG leads, and 15° to around 165° from the corresponding second one or more ECG leads.

In an aspect, the wearable medical device may further include an output device configured to output a notification to the patient to cause the one or more portions of one or more arms of the patient to contact the one or more touch electrodes.

In an aspect, the wearable medical device may further include an output device, where the at least one processor is configured to detect when a first electrode of the one or more touch electrodes is contacted with one or more portions of one or more arms of the patient, and cause, responsive to detection, the output device to output a message to the patient.

In some implementations, the second one or more ECG leads provides different ECG signal characteristics relative to the first one or more ECG leads.

In some implementations, the second one or more ECG leads provides better P-wave characteristics relative to the first one or more ECG leads.

In some implementations, the better P-wave characteristics includes greater P-wave signal amplitudes in the second one or more ECG leads relative to the first one or more ECG leads.

In some implementations, the second one or more ECG leads provides one or more of better R-wave characteristics, lower signal artifacts, and better heart rate detection characteristics relative to the first one or more ECG leads.

In some implementations, the at least two ECG electrodes are located on a left side of the patient's chest; and the one or more touch electrodes is configured to be contacted by a portion of either the right arm or the left arm of the patient.

In some implementations, the at least two ECG electrodes are located on either anterior or lateral thorax locations of the patient; and the one or more touch electrodes is configured to be contacted by a portion of either the right arm or the left arm of the patient.

In some implementations, the at least two ECG electrodes are located on one or more of a left mid-clavicular region, a left mid-axillary region, a right mid-clavicular region, and a right mid-axillary region of the patient; and the one or more touch electrodes is configured to be contacted by a portion of either the right arm or the left arm of the patient.

In some implementations, at least one of the at least two ECG electrodes is located within a left lower thoracic quadrant of the patient; and a first ECG lead of the second one or more ECG leads is within 15° of a standard Lead II in accordance with a standard 12 lead ECG system.

In some implementations, at least one of the at least two ECG electrodes is located within a left lower thoracic quadrant of the patient; and a first ECG lead of the second one or more ECG leads is within 15° of a standard Lead I in accordance with a standard 12-lead ECG system.

In an aspect, the wearable medical device may further include an adhesive layer coupled to at least one of the first side of the substrate and the at least two ECG electrodes and adapted to secure the wearable medical device to the skin of the patient.

In an aspect, the wearable medical device may further include an acoustic transducer in communication with the at least one processor and configured to detect one or more vibrations of the patient.

In an aspect, the wearable medical device may further include communications circuitry for receiving instructions from a remote server, and for transmitting the ECG lead data to the remote server.

In some implementations, the one or more touch electrodes includes one or more projecting members adapted to at least partially penetrate the epidermis of a respective finger of the patient.

In an aspect, the wearable medical device may further include a vibrating element to promote contact between the one or more touch electrodes and the epidermis of a respective finger of the patient.

In one aspect, embodiments of a wearable medical device for monitoring a cardiac condition of a patient, includes a plurality of ECG electrodes disposed in spaced apart positions about a torso of a patient and configured to be in continuous contact with skin of the patient; one or more touch electrodes configured to be contacted with one or more portions of one or more arms of the patient; ECG circuitry in communication with the plurality of ECG electrodes and the one or more touch electrodes; a memory in communication with the ECG circuitry; and at least one processor in communication with the memory and the ECG circuitry, the at least one processor configured to receive a first set of electrical signals from the plurality of ECG electrodes, generate first one or more ECG leads from the received first set of electrical signals, receive a second set of electrical signals from a predetermined combination of the plurality of ECG electrodes and the one or more touch electrodes when the one or more touch electrodes is contacted with one or more portions of one or more arms of the patient, generate second one or more ECG leads from the received second set of electrical signals, and store ECG lead data corresponding the first one or more ECG leads and the second one or more ECG leads in the memory.

In some implementations, the one or more touch electrodes includes a single touch electrode that is configured to be contacted with a finger of the right or left arm of the patient.

In some implementations, the one or more touch electrodes includes two touch electrodes that are configured to be contacted with a left finger of the left arm of the patient and a right finger of the right arm of the patient respectively.

In some implementations, the first one or more ECG leads are each separated by at least 15° from a corresponding second one or more ECG leads in a vector cardiogram representation of the first one or more ECG leads and the second one or more ECG leads.

In an aspect, the wearable medical device may further include an output device configured to output a notification to the patient to cause the one or more portions of one or more arms of the patient to contact the one or more touch electrodes.

In an aspect, the wearable medical device may further include an output device, where the at least one processor is configured to detect when a first electrode of the one or more touch electrodes is contacted with one or more portions of one or more arms of the patient, and cause, responsive to detection, the output device to output a message to the patient.

In an aspect, the wearable medical device may further include an output device configured to output a message to the patient when the one or more touch electrode is contacted with one or more portions of one or more arms of the patient.

In some implementations, the second one or more ECG leads provides different ECG signal characteristics relative to the first one or more ECG leads.

In some implementations, the second one or more ECG leads provides better P-wave characteristics relative to the first one or more ECG leads.

In some implementations, the better P-wave characteristics includes greater P-wave signal amplitudes in the second one or more ECG leads relative to the first one or more ECG leads.

In some implementations, the second one or more ECG leads provides one or more of better R-wave characteristics, lower signal artifacts, and better heart rate detection characteristics relative to the first one or more ECG leads.

In some implementations, the plurality of ECG electrodes is located on a left side of the patient's chest; and a first touch electrode of the one or more touch electrodes is configured to be contacted by a portion of either the right arm or the left arm of the patient.

In some implementations, the plurality ECG electrodes is located on either anterior or lateral thorax locations of the patient; and a first touch electrode of the one or more touch electrodes is configured to be contacted by a portion of either the right arm or the left arm of the patient.

In some implementations, the plurality ECG electrodes is located on one or more of a left mid-clavicular region, a left mid-axillary region, a right mid-clavicular region, and a right mid-axillary region of the patient; and a first touch electrode of the one or more touch electrodes is configured to be contacted by a portion of either the right arm or the left arm of the patient.

In some implementations, at least one of the plurality of ECG electrodes is located within a left lower thoracic quadrant of the patient; and a first ECG lead of the second one or more ECG leads is within 15° of lead II in accordance with a standardized 3-lead ECG.

In some implementations, at least one of the plurality of ECG electrodes is located within a left lower thoracic quadrant of the patient; and a first ECG lead of the second one or more ECG leads is within 15° of lead I in accordance with a standardized 3-lead ECG.

In an aspect, the wearable medical device may further include an adhesive layer coupled to at least one of the first side of the substrate and the plurality of ECG electrodes and adapted to secure the wearable medical device to the skin of the patient.

In an aspect, the wearable medical device may further include an acoustic transducer in communication with the at least one processor and configured to detect one or more vibrations of the patient.

In an aspect, the wearable medical device may further include communications circuitry for receiving instructions from a remote server and for transmitting the ECG lead data to the remote server.

In some implementations, the one or more touch electrodes includes one or more projecting members adapted to at least partially penetrate the epidermis of a respective finger of the patient.

In an aspect, the wearable medical device may further include a vibrating element to promote contact between the one or more touch electrodes and the epidermis of a respective finger of the patient.

In one aspect, embodiments of a wearable medical device for monitoring a cardiac condition of a patient, includes a garment worn about the torso of the patient, the garment having an inner side and an outer side opposite the inner side; a plurality of ECG electrodes disposed on the inner side of the garment and configured to be in continuous contact with skin of the patient; one or more touch electrodes disposed on the outer side of the garment and configured to be contacted with a portion of an arm of the patient; ECG circuitry in communication with the plurality of ECG electrodes and one or more touch electrodes; a memory in communication with the ECG circuitry; and at least one processor in communication with the memory and the ECG circuitry, the at least one processor configured to receive a first set of electrical signals from the plurality of ECG electrodes, generate first one or more ECG leads from the received first set of electrical signals, detect an abnormal rhythm in the patient based on the first one or more ECG leads, receive a second set of electrical signals from a predetermined combination of the plurality of ECG electrodes and the one or more touch electrodes when the one or more touch electrodes is contacted with one or more portions of one or more arms of the patient, generate second one or more ECG leads from the received second set of electrical signals, and confirm whether the detected abnormal rhythm in the patient includes an arrhythmia condition in the patient based at least in part on the second one or more ECG leads.

In some implementations, the one or more touch electrodes includes a single touch electrode that is configured to be contacted with a finger of the right or left arm of the patient.

In some implementations, the one or more touch electrodes includes two touch electrodes that are configured to be contacted with a left finger of the left arm of the patient and a right finger of the right arm of the patient respectively.

In some implementations, the first one or more ECG leads are each separated by at least 15° from a corresponding second one or more ECG leads in a vector cardiogram representation of the first one or more ECG leads and the second one or more ECG leads.

In an aspect, the wearable medical device may further include an output device configured to output a notification to the patient to cause the one or more portions of one or more arms of the patient to contact the one or more touch electrodes.

In an aspect, the wearable medical device may further include an output device, where the at least one processor is configured to detect when a first electrode of the one or more touch electrodes is contacted with one or more portions of one or more arms of the patient, and cause, responsive to detection, the output device to output a message to the patient.

In some implementations, the second one or more ECG leads provides different ECG signal characteristics relative to the first one or more ECG leads.

In some implementations, the second one or more ECG leads provides better P-wave characteristics relative to the first one or more ECG leads.

In some implementations, the better P-wave characteristics includes greater P-wave signal amplitudes in the second one or more ECG leads relative to the first one or more ECG leads.

In some implementations, the second one or more ECG leads provides one or more of better R-wave characteristics, lower signal artifacts, and better heart rate detection characteristics relative to the first one or more ECG leads.

In some implementations, at least one of the plurality of ECG electrodes is located within a left lower thoracic quadrant of the patient; and a first ECG lead of the second one or more ECG leads is within 15° of a standard Lead II in accordance with a standard 3-lead ECG system.

In some implementations, at least one of the plurality of ECG electrodes is located within a left lower thoracic quadrant of the patient; and a first ECG lead of the second one or more ECG leads is within 15° of a standard Lead I in accordance with a standard 3-lead ECG system.

In an aspect, the wearable medical device may further include an acoustic transducer in communication with the at least one processor and configured to detect one or more vibrations of the patient.

In an aspect, the wearable medical device may further include communications circuitry for receiving instructions from a remote server and for transmitting ECG lead data to the remote server, where confirming includes providing ECG lead data to the remote server and receiving an analysis result.

In some implementations, the one or more touch electrodes includes one or more projecting members adapted to at least partially penetrate the epidermis of a respective finger of the patient.

In an aspect, the wearable medical device may further include a vibrating element to promote contact between the one or more touch electrodes and the epidermis of a respective finger of the patient.

In an aspect, the wearable medical device may further include a user interface, where at least a first touch electrode of the one or more touch electrodes is disposed on a housing of the user interface.

In some implementations, the at least one processor is further configured to, after confirming the detected abnormal rhythm in the patient includes the arrhythmia condition, activate delivery of a therapy to the patient.

In an aspect, the wearable medical device may further include at least two therapy electrodes electrically coupled to at least one defibrillator component, where delivery of the therapy includes delivery of a defibrillation shock.

In some implementations, the one or more touch electrodes couple to the garment using snaps.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Overview

Figure 1A:
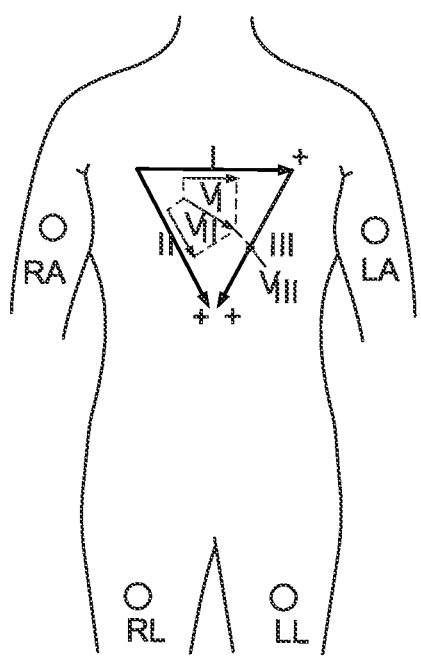
FIG. 1A depicts a basic Einthoven diagram composed of three electrodes, where each pair of electrodes forms a lead that can describe electrical activity of a heart from a particular angle according to an example.

During each heartbeat, a healthy heart has an orderly progression of electrical depolarization that can be detected as a characteristic ECG tracing. This ECG tracing conveys information about the structure of the heart and the function of its electrical conduction system. FIG. 1A depicts a basic Einthoven diagram representation using standardized 3-lead ECG formed from three electrodes. Each pair of electrodes forms a lead. The ECG leads can in turn be represented as vectors in a vectorcardiogram representation of the electrical activity of the heart. An ECG vector has an orientation, a magnitude, and a sense that can describe the electrical activity of the heart from a particular angle.

Figure 1B:
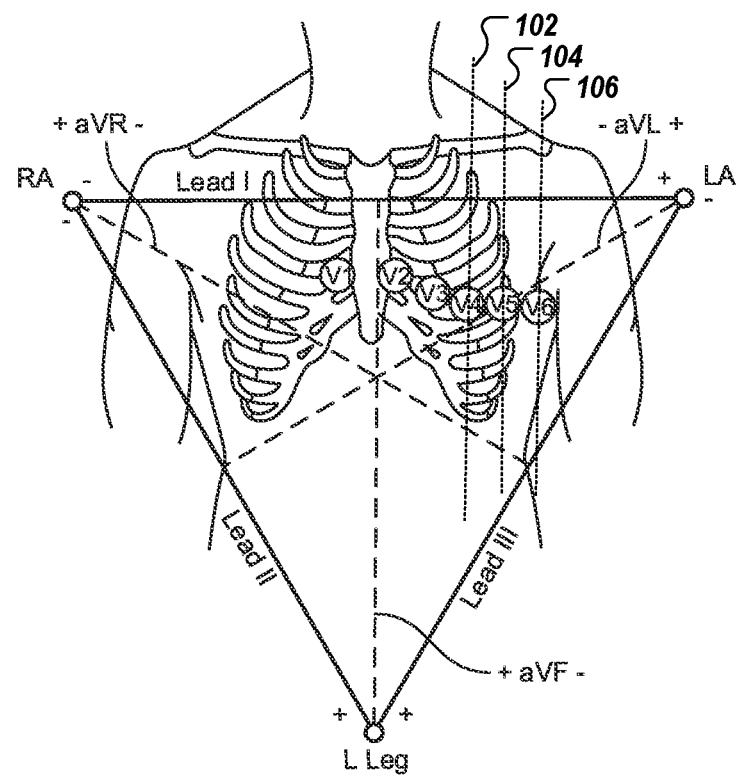
FIG. 1B depicts a standard Einthoven diagram composed of ten electrodes that form 12 standard leads at well-established anatomical locations.

FIG. 1B depicts a standard Einthoven diagram composed of ten electrodes that form a 12-lead standard ECG at well-established anatomical locations. The ten electrodes of the 12-lead standard ECG are positioned at: Right Arm (RA), Right Leg (RL), Left Arm (LA), Left Leg (LL), fourth intercostal space on the right sternum ($V_1$), fourth intercostal space at the left sternum (V2), midway between placement of V2 and V4 (V3), fifth intercostal space at the midclavicular line (V4), anterior axillary line on a same horizontal level as V4 (V5), and at mid-axillary line on a same horizontal level as V4 and V5 (V6). Readings from the standard 12 lead ECG are used as a benchmark for common clinical practice. However, patients seldom are fitted with a cardiac monitor using the 12-lead standard ECG. Outpatient continuous cardiac monitors typically only include several electrodes which are intended for monitoring specific cardiac conditions.

Figure 1C:
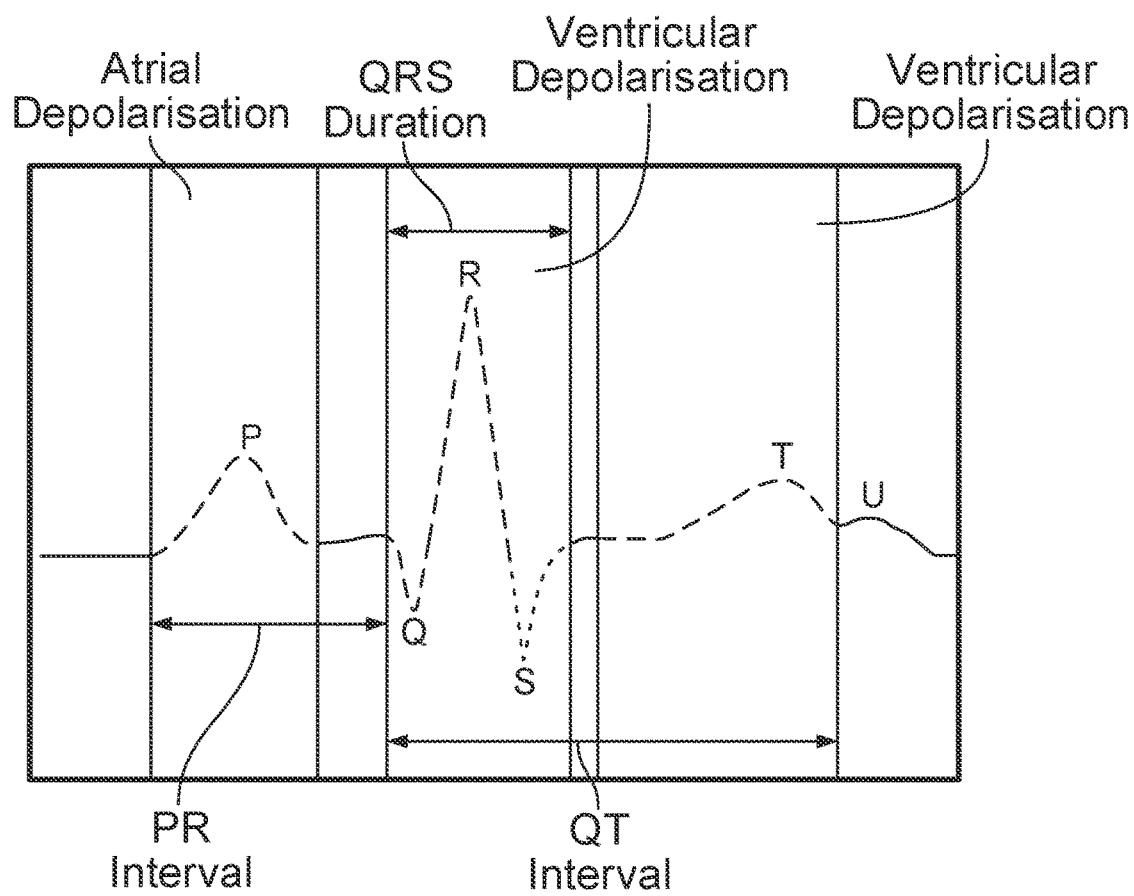
FIG. 1C depicts an example ECG of normal sinus rhythm and respective stages of activation and recovery of a heart wave.
Figure 1C:
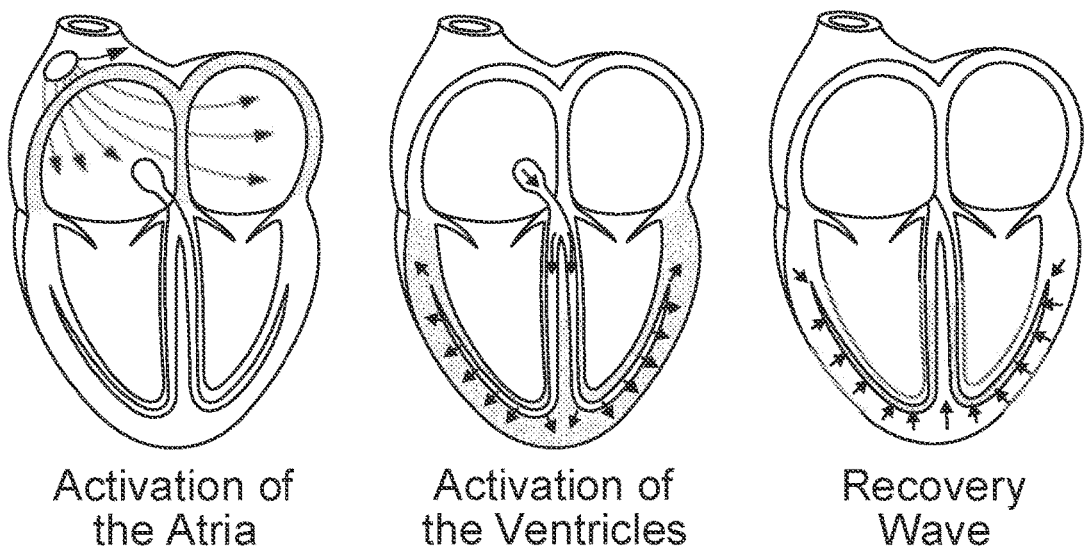

An example ECG of normal sinus rhythm detected with Lead I and respective stages of activation and recovery of a heartbeat is depicted in FIG. 1C. During atrial depolarization of the myocardium, activation of the atria can form a dipole that can be detected as a P-wave picked up by Lead I. The P-wave forms a temporal association between impulse transmission and conduction of the myocardium. Initially, the sinoatrial node depolarizes, an impulse arrives in the AV node, the impulse passes the bundle of His, the impulse then passes the bundle branches, and the Purkinje fibers. During ventricular depolarization, activation of the ventricles can form a dipole that can be detected as a QRS-wave picked up by Lead I. During recovery, ventricular repolarization can form a dipole that can be detected as a T and U wave and picked up by the Lead I as shown in FIG. 1C.

Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators (such as manual defibrillators or automated external defibrillators (AEDs)) have significantly improved the ability to treat these otherwise life-threatening conditions. Such devices operate by applying corrective electrical pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns. Prompt cardiac data from cardiac monitoring devices are an essential component used in decision making done by ICD's and AEDs to provide an intervention.

Example external cardiac monitoring and/or treatment devices include cardiac monitors such as the ZOLL Cardiac Monitor, the ZOLL LifeVest® wearable cardioverter defibrillator, and the AED Plus, all available from ZOLL Medical Corporation (Chelmsford, MA).

This disclosure relates to wearable medical devices for releasably mounting to a patient's chest each including at least two skin-facing electrodes for ongoing monitoring of heart functioning and at least one externally facing finger placement or touch electrode for optionally obtaining additional circuit vectors for deriving additional metrics regarding the functioning of the patient's heart. As discussed in relation to FIGS. 1A-C, standard ECG leads/vectors are established by placement of ECG electrodes at specific locations on the body of the patient in relation to the heart. For example, the at least two skin-facing electrodes can be located at two or more of the standard anatomical locations in accordance with a predetermined standard ECG system. For example, the standard ECG system can be the 12 lead ECG system described above, and the one or more leads of the device can be any one of the 12 leads as shown in Table 1 below.

TABLE 1

| Lead Reference | Lead type | Lead derivation from electrodes |
| --- | --- | --- |
| I | Limb lead | LA-RA |
| II | Limb lead | LL-RA |
| III | Limb lead | LL-LA |
| aVR | Augmented lead | RA-(LA + LL)/2 |
| aVL | Augmented lead | LA-(RA + LL)/2 |
| aVF | Augmented lead | LL-(RA + LA)/2 |
| $V_1$ | Precordial lead | $V_1$-(RA + LA + LL)/3 |
| $V_2$ | Precordial lead | $V_2$-(RA + LA + LL)/3 |
| $V_3$ | Precordial lead | $V_3$-(RA + LA + LL)/3 |
| $V_4$ | Precordial lead | $V_4$-(RA + LA + LL)/3 |
| $V_5$ | Precordial lead | $V_5$-(RA + LA + LL)/3 |
| $V_6$ | Precordial lead | $V_6$-(RA + LA + LL)/3 |

The skin-facing ECG electrodes of the medical device can be located at one or more of any one of the following standard anatomical locations: Right Arm (RA), Right Leg (RL), Left Arm (LA), Left Leg (LL), fourth intercostal space on the right sternum ($V_1$), fourth intercostal space at the left sternum ($V_2$), midway between placement of $V_2$ and $V_4$ ($V_3$), fifth intercostal space at the midclavicular line ($V_4$), anterior axillary line on a same horizontal level as $V_4$ ($V_5$), and at mid-axillary line on a same horizontal level as $V_4$ and $V_5$ ($V_6$). These anatomical locations are shown in FIGS. 1A-B, and described in Table 2 below.

TABLE 2

| Electrode name | Description of standard anatomical location |
| --- | --- |
| RA | On the right arm, avoiding thick muscle. |
| LA | In the same location where RA was placed, but on the left arm. |
| RL | On the right leg, lower end of medial aspect of calf muscle. (Avoid bony prominences) |
| LL | In the same location where RL was placed, but on the left leg. |
| V1 | In the fourth intercostal space (between ribs 4 and 5) just to the right of the sternum (breastbone). |
| V2 | In the fourth intercostal space (between ribs 4 and 5) just to the left of the sternum. |
| V3 | Between leads V2 and V4. |
| V4 | In the fifth intercostal space (between ribs 5 and 6) in the mid-clavicular line. |
| V5 | Horizontally even with V4, in the left anterior axillary line. |
| V6 | Horizontally even with V4 and V5 in the midaxillary line. |

For purposes of discussion, an example standard lead system is shown as the 12 lead ECG system above. Other standard ECG lead systems can include a 3 lead ECG system, or a 5 lead ECG system. For example, the 3 lead ECG system can include 3 or 4 ECG electrodes. These electrodes are located as follows: Right Arm (RA), Left Arm (LA), Left Leg (LL), and Right Leg (RL). These leads can provide information for basic heart rhythm monitoring but not for certain specialized features. For example, a specialized feature such as ST segment elevation may not be picked up by a 3 lead ECG system. This is because the three leads do not provide adequate information about the anterior wall of the heart. For example, the 5 lead ECG system can use 4 extremity leads and one percordial lead. In implementations, the 5 electrodes include Right Arm (RA), Left Arm (LA), Right Leg (RL), Left Leg (LL), and one precordial chest electrode ($V_1$). In certain standard 5 ECG lead systems, the $5^{th}$ lead electrode can be changed. For example, the lead V1 can be changed to lead V5 to monitor lateral left ventricle and atrium when suspecting certain arterial problems in the patient's heart. For example, the electrode for lead V5 can be placed at or just below the $5^{th}$ intercoastal space at the anterior axillary line (See, e.g., FIG. 1B).

In some implementations, the skin-facing electrodes may be positioned in accordance with one or more non-standard ECG leads. For example, non-standard leads include one or more leads that do not correspond to any of the 12 standard ECG leads listed in Table 1. For example, in certain implementations, the non-standard leads when represented as vectors in a vectorcardiogram may be within 15° of any of the standard ECG leads. In some implementations, the skin-facing electrodes may be located at anatomical sites on the left or right side of the patient's upper torso. For instance, the two electrodes may be positioned within the left upper thoracic quadrant, which runs from the middle axillary line to the anterior (midsternal) median line and is above the xiphoid process. In such locations, the skin-facing electrodes forms a non-standard ECG lead for monitoring the electrical activity of the heart. In some examples, the skin-facing electrodes may be located on the left or right side of the patient's upper torso along the midclavicular line. In other examples, the skin-facing ECG electrodes can be located on one or more of a left mid-clavicular region, a left mid-axillary region, a right mid-clavicular region, and a right mid-axillary region of the patient as described in further detail below (see, e.g., FIGS. 4A and B). Having non-standard placement of electrodes as described above, the medical device, in some implementations, is configured to identify one or more non-standard ECG vectors and to determine, based on sensed ECG data, a first one or more ECG leads for continuous monitoring of the patient's heart activity. The ECG leads can be represented as vectors in a vectorcardiogram representation of the electrical activity of the heart. Each externally facing touch electrode is configured to form an additional ECG lead when contacted that has either a larger amplitude value than some or all or the first one or more ECG leads and/or separated by at least 15° (e.g., between around 15° and around 90°, between around 15° and around 120°, between around 15° and around 135°, and between around 15° and around 165°, including angles therebetween) from some or all of the first one or more ECG leads. Further, in some implementations, an ECG lead formed between the touch electrode and one or more of the skin-facing electrodes may be within 15° of one or more leads of the standard 12 lead ECG system. For instance, the ECG lead formed between the touch electrode and a first one of the skin-facing electrodes may be within 15° of a standard Lead I or Lead II of the 12 lead ECG system. In certain implementations, the least two skin-facing electrodes can be disposed in spaced apart positions about a torso of a patient and the at least one externally facing touch electrode (e.g., affixed to a garment) can be configured to be contacted with one or more portions of one or more arms of the patient.

Figure 1D:
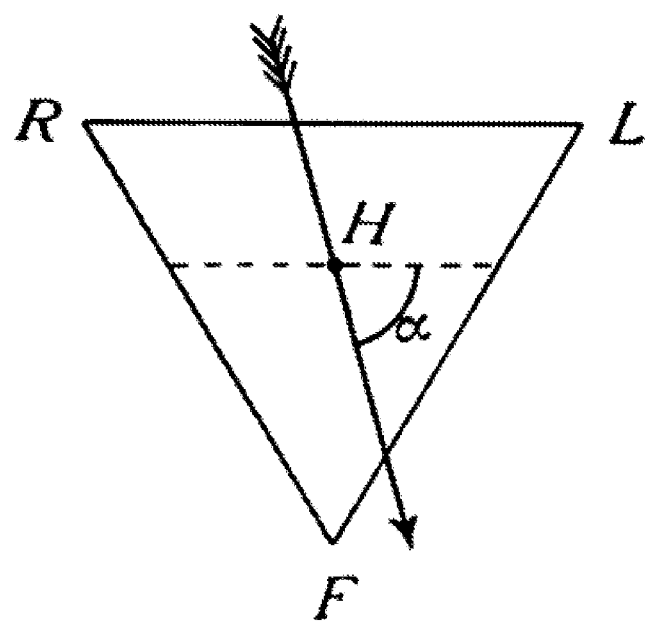
FIG. 1D shows a graphical example of a mean vector of the QRS complex as projected on to a frontal plane.

As noted above, an ECG vector as described herein is a mathematical representation of an average electrical signal activity of the heart and has orientation, magnitude, and sense. Electric forces from the heart as recorded from the surface of the human body can be represented as a vector force. The equilateral triangle of Einthoven can be used to obtain a mean electric axis of the QRS complex of a recorded electrocardiogram from standard limb leads I, II, and III. Einthoven's illustration of the mean vector as projected on to a frontal plane formed from standard limb Leads I, II, and III is shown in FIG. 1D, where R represents the patient's right arm, L represents the patient's left arm, and F represents the patient's foot. The angle ($\alpha$) of the vector (H) indicates the orientation of the mean vector and the length of the vector indicates the mean magnitude. Further, the sense of the vector is indicated by the arrow showing that the vector is directed away from the area of greatest relative negativity of the electric force derived from the heart toward the area of greatest relative positivity. Similar principles can be applied to the T wave, the electric force of repolarization of the ventricles, and to the P wave, the electric force of depolarization of the atria.

Figure 1E:
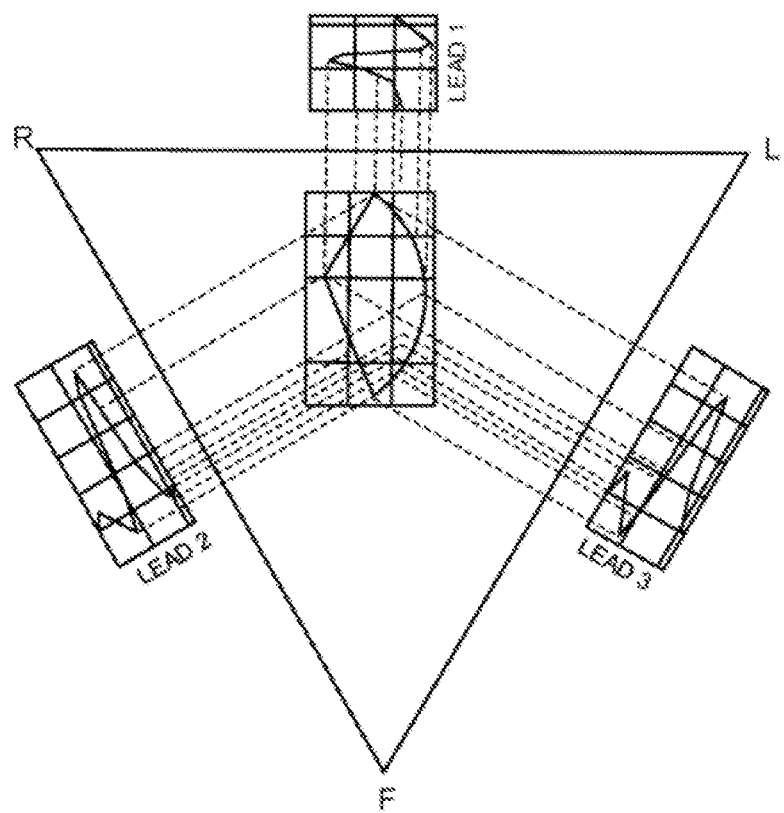
FIG. 1E is a graphical example of a monocardiogram, also known as a spatial vectorcardiogram, spatial VCG, or VCG.

A vector loop can be used to represent a continuous uninterrupted series of vector, for example, to display as vector quantities the electric forces of depolarization and repolarization from body surface recordings of electric cardiac activity noted in an electrocardiogram. For example, a loop can be constructed by projecting the time-varying ECG leads onto a common plane as shown in FIG. 1E. Various lead configurations can be used to measure and analyze electrical events. In some situations, three leads can be designed to record components of a resultant cardiac electromotive force in three mutually perpendicular directions, thus solving the problem of deriving the resultant cardiac electromotive force. As one example, the potential measured by any electrocardiographic lead is represented by V and the resultant cardiac electromotive force is denoted by H or the heart vector. Mathematically, V=H·L where L is the vector representing the strength of the lead being used to measure the potential. According to mathematic principles, the dot product of two vectors is a scalar, i.e. potential or voltage does not have an associated direction but only a magnitude whereas the heart vector H and the lead vector L each has its own direction. This basic rule of vector mathematics can also be expanded to the following: $V=H_xL_x+H_yL_y+H_zL_z$, where $H_x$, $H_y$, $H_z$ are the three components of the heart vector and $L_x$, $L_y$, $L_z$ are the three components of the lead vector. Thus, to measure the component of the heart vector in the X direction, a lead can be designed that has components ($L_x$, 0, 0). In that case $V_x=H_xL_x$, if the strength $L_x$ of the lead is known, upon measuring the potential $V_x$, $H_x$ can be calculated.

Figure 1F:
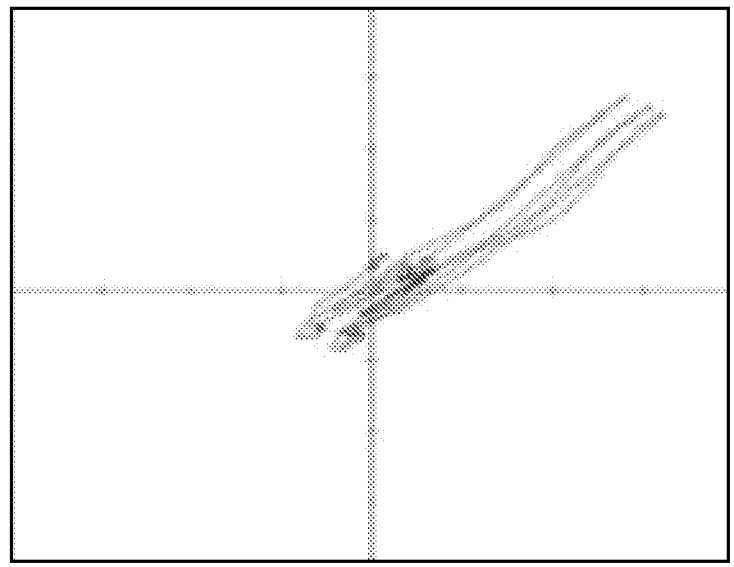
FIG. 1F shows an overlay of several vector loops for a baseline VCG recorded from a patient whose rhythm is a normal sinus rhythm.
Figure 1G:
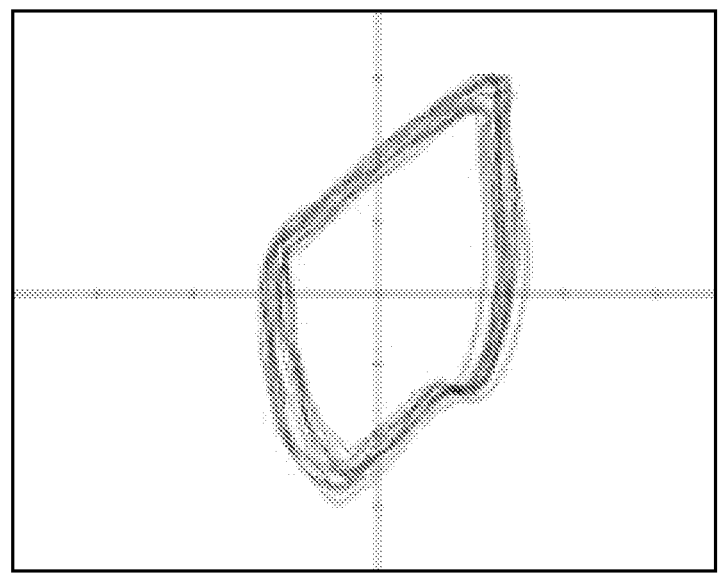
FIG. 1G shows an overlay of several vector loops recording several hours later from the patient of FIG. 1F.

A number of different electrode configurations exist that provide a means for generating orthogonal leads, though most often the full X, Y, and Z orthogonal leads of VCG are used. Some examples of these are the Grishman, Milnor, Wilson-Burch, Frank, Dower and the standard 12 lead configuration well-known in clinical practice from which the orthogonal lead set can be derived. In these cases these "orthogonal" leads are approximations of orthogonal leads. As used herein, "orthogonal" leads encompass both true leads as well as broader approximations of orthogonal leads. In some versions of orthogonal lead generation, two approximately orthogonal leads may be used to generate a VCG along one plane (e.g., two electrodes placed anterior-posterior to generate the X lead of the VCG, and two electrodes placed lateral-lateral on the mid-axillary line to generate the Y lead of the VCG) from which the vector loops in the X-Y projection plane can be generated. Referring to FIGS. 1F and 1G, FIG. 1F shows an overlay of several vector loops for a baseline VCG recorded from a patient whose rhythm is a normal sinus rhythm, for instance upon the initial fitting and setup of a wearable defibrillator (e.g., LifeVest® by ZOLL Medical Corporation of Pittsburgh, PA). FIG. 1G shows an overlay of several vector loops recording several hours later from the same patient. In this case, the ECG of the patient has degenerated into a life-threatening arrhythmia, e.g. a ventricular tachycardia (VT). Vector loop analysis via shape or other means can be very helpful in distinguishing between healthy ECG rhythms and life-threatening arrhythmias such as VT or ventricular fibrillation (VF), or in detecting when the risk of a medical event occurring at some time in the future is elevated, such as is described in U.S. Pat. No. 9,545,209B2, "VCG Vector Loop Bifurcation", or U.S. Patent application US20160135706A1, "Medical Premonitory Event Estimation", which are hereby incorporated by reference in their entireties. For example, the one or more ECG leads described herein, including the ECG leads generated via the touch electrode can be used to derive one or more ECG loops similar to those shown in FIGS. 1F and 1G. As shown, in the short term (e.g., over a period of several successive cardiac cycles) changes in a patient's vector loop from a baseline loop can be helpful in determining life-threatening arrhythmias such as VT or ventricular fibrillation (VF).

Over a longer-term period (e.g., over a week, month, several months, or even years), more gradual changes in the vector loop can indicate that the risk of a medical event occurring at some time in the future has been elevated. As a specific example, in one implementation, a patient wearing the medical device may periodically contact the touch electrode in a manner described in detail herein. Each time, the medical device may record an ECG lead of the patient and augment a vector loop with the additional information. Over time, the medical device may monitor for significant deviations in the trajectory of the loop relative to a baseline or averaged loop of the patient. For example, a variation of the loop trajectory from a baseline trajectory that occurs for a portion of the ECG signal can be based on the variation exceed a predetermined standard deviation. As another example, one or more statistical analysis methods can be used to identify such deviations. For example, a non-Gaussian statistical analysis can be implemented to monitor for such deviations.

Adding one or more leads to single lead ECG monitoring can enhance the diagnostic accuracy of both automated algorithms and manual clinician diagnosis. The enhanced diagnostic accuracy can either result from using the additional leads to create a vector loop, or alternatively performing scalar measures such as ST elevation, QRS width, etc. on multiple leads. The addition of leads can require more cumbersome, larger, heavier wearable medical devices incorporating ECG monitoring. The extra leads may be detrimental to the patient's mobility and comfort due to the added bulk and weight and may lead to degradation in patient compliance with wearing the device, resulting in loss of protection of the patient's health.

Example Medical Devices

FIGS. 2A-2F illustrate examples of a medical device 200a-f that is external, ambulatory, and wearable by a patient, and configured to perform one or more processes described herein. For example, the medical device 200a-f can be a non-invasive medical device configured to be located substantially external to the patient. For instance, a medical device that is substantially external as described herein can include externally worn or carried devices (e.g., for monitoring and/or treating cardiac arrhythmias) that includes a drug infusion element a portion of which may be subcutaneously implanted in the patient for continuous or periodic administration of one or more drugs to the patient. Such a medical device 200a-f can be an ambulatory medical device that is, for example, capable of and designed for moving with the patient as the patient goes about his or her daily routine. In an example, the medical device 200a-f can be configured for releasably mounting to a patient's chest.

The medical device 200a-f, in some implementations, includes a substrate 210, at least two ECG electrodes 220a-b, and one or more touch electrodes 230 and/or one or more touch electrodes 232 having a number of projections 234. Further, the medical device 200a-f may include or be in communication with ECG circuitry, a medical device controller, a memory, at least one processor, an antenna, a patient interface including one or more response button(s), a transducer 250, a vibrating element 260, a battery or any combination of these. For example, the controller, memory, and at least one processor for processing signals collected by the medical device 200a-f may be provided in a separate housing in wired or wireless communication with the medical device 200a-f. A portion of the components of the medical device 200a-f, in some embodiments, are affixed to the substrate 210 or permanently integrated into the substrate 210.

In some embodiments, ECG circuitry is operatively coupled to the at least two ECG electrodes 220, which are disposed on a first side of the substrate 210 and configured to be in continuous contact with skin of the patient. This continuous contact, for example, may provide the opportunity to develop one or more ECG leads from the ECG electrode 220 signals to continuously monitor the patient. The ECG circuitry, in some examples, may be disposed within the substrate 210, affixed to the substrate 210, or in communication with the ECG electrodes 220 while being positioned in a remote unit. The remote unit may be in wired or wireless communication with the ECG electrodes 220.

In some implementations, an adhesive layer 240 is affixed to the first side of the substrate 210 and/or to the at least two ECG electrodes 220a-b. The adhesive layer 240, for example, may be adapted to secure the wearable medical device to the skin of the patient, maintaining contact between the ECG electrodes 220a-b and position of the device upon the patient's chest. In some embodiments, the medical device 200a-f is maintained upon the patient's chest by the adhesive layer 240 without additional securing mechanisms. In other embodiments, securing mechanisms, such as a bandolier harness, medical tape, and/or a flexible medical wrap, aid in maintaining position of the medical device 200a-f. The skin-facing ECG electrodes 220a-b can include a layer of conductive gel to improve the electrode-skin impedance characteristics. For example, the conductive gel is configured for continuous and/or long-term use by the patient. In this regard, the conductive gel may be formed from a hydrogel or other material that provides for the passage of patient skin moisture to promote breathability and thus patient comfort. The conductive gel may include, for example, the gels described in U.S. Pat. No. 9,737,701 titled "Long term wear multifunction biomedical electrode," which is hereby incorporated herein by reference in its entirety. Other examples of conductive gels include FW266 hydrogel, FW350 hydrogel, FW340 BD hydrogel, and FW340 hydrogel all available from First Water Limited, and Promeon RD-63B hydrogel, available from Tyco Healthcare Group (d/b/a/Covidien). In some examples, suitable hydrogels of which the conductive gel may be comprised include the materials described in U.S. Pat. No. 9,867,976 titled "Long-term wear electrode", which is hereby incorporated herein by reference in its entirety.

The ECG circuitry, in some implementations, is further operatively coupled to the one or more touch electrodes 230 disposed on a second side of the substrate 210 and configured to be contacted with one or more portions of one or more arms of the patient, such as, in some examples, one or more fingers, a portion of the palm, or a wrist region of the patient. In a particular example, each of the one or more touch electrodes 230 is configured to be contacted with a finger of the right or left hand of the patient. The at least one touch electrode 230, 232 is configured for obtaining one or more additional circuit vectors through generating additional leads for ECG monitoring by the ECG circuitry. For example, upon positioning of the patient's finger, hand, or arm portion upon a given touch electrode 230, 232, the ECG circuitry may proceed to monitor additional leads provided through the contact.

The medical device controller, in some implementations, communicates with the ECG circuitry and includes one or more of the memory and processing circuitry including the at least one processor. The medical device controller can be operatively coupled to the at least two ECG electrodes 220a-b and the one or more touch electrodes 230 with the ECG circuitry. Other aspects of an example of the medical device controller are described in relation to FIG. 8 below.

Figure 2A:
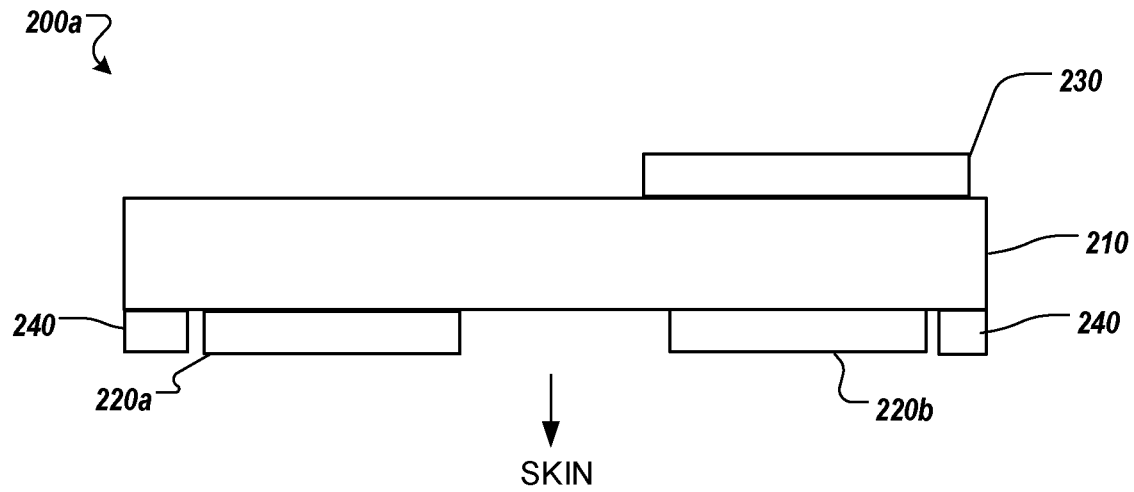
FIGS. 2A and 2B depict example wearable medical devices for releasably mounting to a patient's chest each including at least two skin-facing electrodes for ongoing monitoring of heart functioning and at least one finger placement electrode for optionally obtaining additional circuit vectors for deriving additional metrics regarding the functioning of the patient's heart.

Turning to FIG. 2A, in some implementations, the medical device 200a includes two ECG electrodes 220a-b on a skin-facing side of substrate 210 and a single touch electrode 230 on the opposite side of substrate 210. The at least two skin-facing electrodes 220a-b are configured to produce a continuous ECG lead/vector for ongoing monitoring of heart functioning via a first one or more standard or non-standard ECG leads. Example standard ECG electrode placement and resulting ECG leads shown in FIGS. 1A-B. Example non-standard ECG electrode placement and resulting ECG leads differ from the standard ECG electrode placement and resulting ECG leads as described above and further illustrated below.

Thus, when the patient contacts a high-input impedance (e.g., >1 MOhm) touch electrode 230, 232, an electrical circuit is created due to the patient's arm acting as a high conductance volume conductor, resulting in a potential at the touch electrode 230, 232 which is a good approximation of the voltage at a location where either the left arm (LA) electrode and/or right arm (RA) electrode is placed in the standard ECG configuration. For instance, by just touching the touch electrode 230, 232 with the patient's right index finger, it is as if an electrode were placed in the standard RA location and connected to the touch electrode 230, 232.

In one example, the medical device 200*a*-*f* may be placed such that the two skin-facing ECG electrodes 220*a*, 220*b* on a skin-facing side of substrate 210 are located at the standard precordial ECG electrode locations of V2 and V4. The ECG circuitry can include one or more ECG monitor circuits, e.g., implemented via integrated heart ECG and rate monitoring chips. For example, a first ECG monitor circuit, such as the integrated heart rate monitor circuit AD8233 ("AD8233") manufactured by Analog Devices, Inc. (Norwood, MA), may be used for amplification of the differential signal between the two skin-facing electrodes 220*a*, 220*b*. The ECG circuitry may also provide signal conditioning such as a high pass filter for DC-offset rejection and a low pass filter for noise rejection and muscle artifact reduction. The ECG circuitry may also provide detection of poor electrical contact also known as lead-off detection. The ECG circuitry may provide detection of poor electrical contact by techniques employing impedance spectroscopy as described in U.S. Pat. No. 9,579,514 to Freeman et al., titled "Impedance spectroscopy for defibrillator applications" and incorporated herein in its entirety (hereinafter, the '514 patent). In particular, as described in the '514 patent, the lead-off detection circuit may implement impedance spectroscopy to determine a transthoracic impedance (TTI) of the patient. For example, the lead-off detection circuit may determine the TTI of the patient via the skin-facing electrodes and monitor for changes in the TTI that may be indicative of poor electrical contact or lead-off. An example TTI process can be as follows. First, an alternating current signal or an alternating voltage signal may be provided to the patient through a pair of the skin-facing electrodes. Based upon the provided signal, a voltage signal or a current signal can be measured by being sensed through the electrodes. Once measured, transthoracic complex impedance can be calculated as a ratio of a provided signal and a measured signal (e.g., a ratio of the provided current signal and the measured voltage signal, or, a ratio of the provided voltage signal and the measured current signal). The transthoracic impedance can then be used for determining a quality of electrical contact of one or more of the skin-facing electrodes. Detection may be accomplished with either one of the skin-facing electrodes 220*a*, 220*b*.

Either one of the skin-facing electrodes may also be connected to a second ECG monitor circuit, such as a second AD8233 chip. When the patient touches the touch electrode, the lead-off detection circuit of the second ECG monitor circuit may indicate to the medical device controller that the touch electrode has been contacted by the patient and that the electrode contacts of both the touch electrode and the skin-facing electrode connected to the second ECG monitor circuit are sufficient to begin to process the ECG data from the second monitor circuit.

Figure 3A:
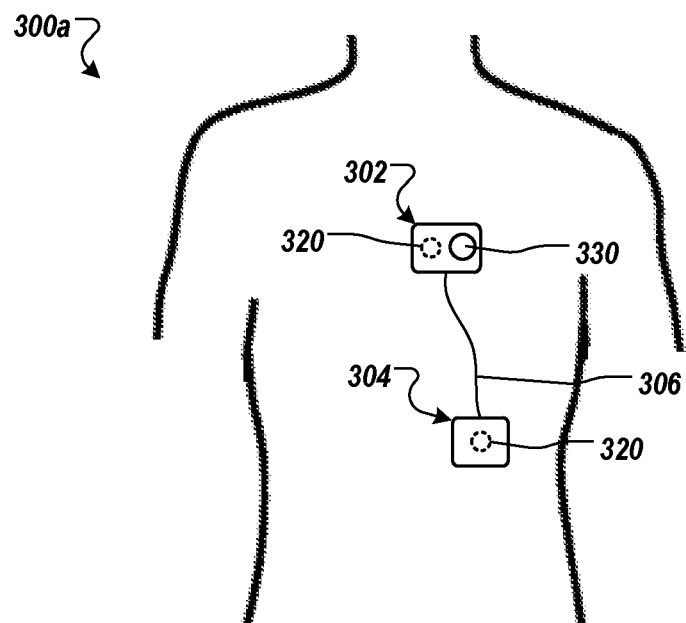
FIGS. 3A and 3B depict example wearable medical devices including two or more ECG electrodes disposed in spaced apart positions about a torso of a patient and configured to be in continuous contact with skin of the patient, one or more touch electrodes configured to be contacted with one or more portions of one or more arms of the patient, and ECG circuitry in communication with the two or more ECG electrodes and the one or more touch electrodes.
Figure 3B:
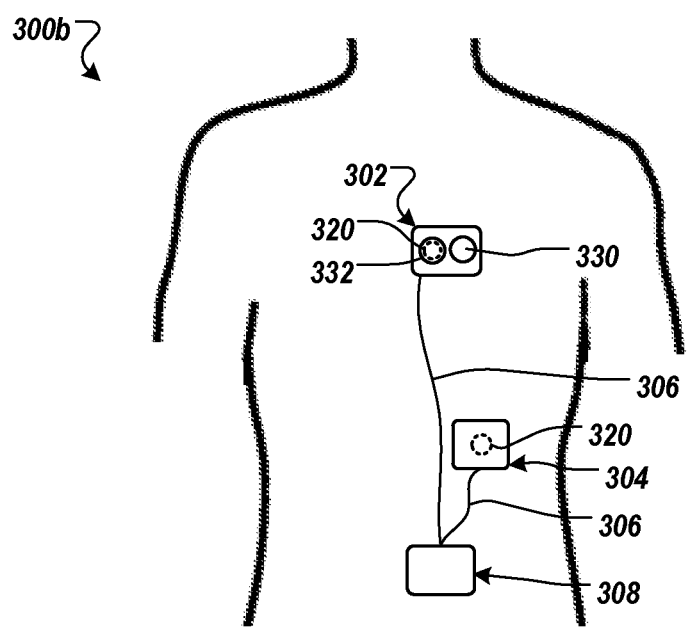

Referring to FIG. 1B, if the skin-facing electrode 220*a*, 220*b* connected to the second ECG monitor circuit is located at the standard V4 precordial electrode position, then the ECG vector generated, although non-standard, can bear some similarities to a standard augmented VL (aVL) ECG vector. The same can be true if the skin-facing electrode 220*a*, 220*b* connected to the second ECG monitor circuit is located at the standard V2 precordial electrode position. Referring to FIGS. 3A and 3B, if the second substrate 304 is positioned such that the skin-facing electrode 320 is in the standard LL (left-leg) ECG electrode position, then the vector generated can be the standard ECG Lead III vector. The ECG electrodes may be placed such that the first ECG monitor circuit generates an ECG lead with a vector angle substantially distinct from a vector angle of the second ECG lead generated by the second ECG monitor circuit. In some implementations, the vector angle is substantially distinct when the vector angle difference is within a range of +15° to 165° or −15° to −165°. Vectorcardiographic analysis can still be performed on any of these vector angle differences that are non-orthogonal.

Figure 4A:
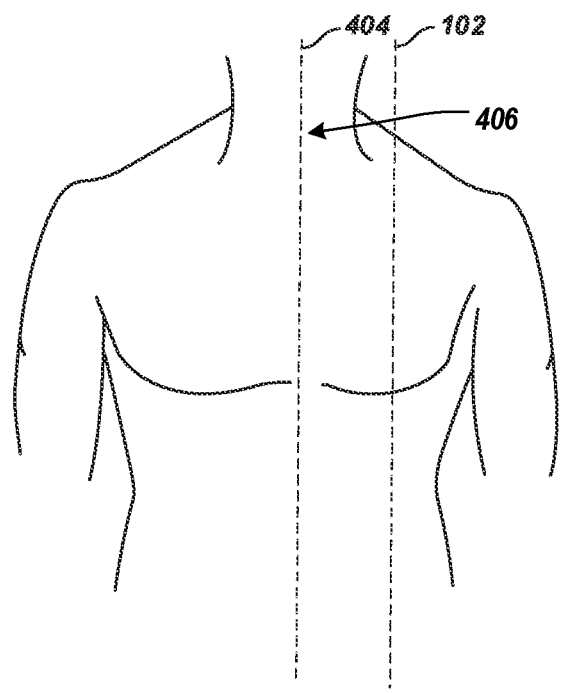
FIGS. 4A, 4B, and 4C depict example positioning of a wearable medical device and example electrode placements for obtaining metrics regarding the functioning of the patient's heart.
Figure 4B:
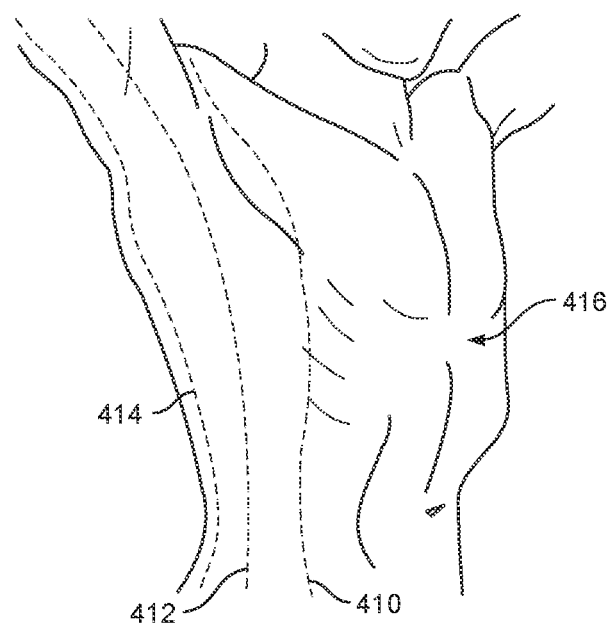
Figure 4C:
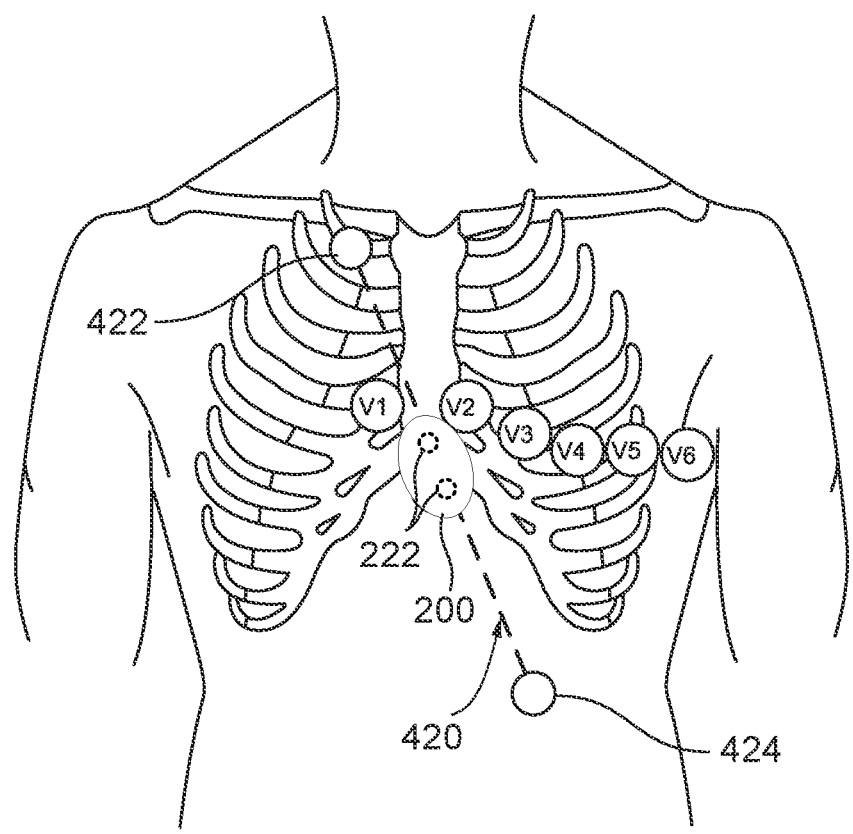

Referring to FIG. 4C, alternatively, the medical device 200 may be placed such that it is configured to be substantially in line with the dotted line 420 defined by sternal clavicular junction (422) and midpoint of the left costal margin in line with the seventh intercostal space (424), for instance, mid-way along the dotted line 420. Such a location can provide a non-standard ECG vector using non-standard ECG electrode locations. For this case, the vector angle difference is approximately orthogonal. For example, referring to FIG. 4C, the medical device 200 can be in the form of a patch with skin-facing ECG electrodes 220/222, described further below. As shown, the medical device 200 can be located equidistant from the sternal clavicular junction 422 and the midpoint of the left costal margin in line with the seventh intercostal space 424 along the dotted line 420. The two skin-facing electrodes 220/222 are aligned along the dotted line 420 from the sternal clavicular junction 422 to the midpoint of the left costal margin in line with the seventh intercostal space 424, generating a first ECG lead. When the patient contacts the touch electrode (not shown for clarity) on the medical device 200 with a portion of their left hand, a second ECG lead is generated based on the touch electrode and at least one of the skin-facing electrodes 220/222. This second ECG lead is substantially orthogonal to the first ECG lead. In this configuration, the ECG leads derived from the medical device 200 can provide orthogonal vectors (e.g., vectors separated by around 90°). Orthogonal vectors can be useful diagnostically as they provide independent views of the electrical activity of the heart.

The teachings of the present disclosure can be generally applied to external medical monitoring and/or treatment devices (e.g., devices that are not completely implanted within the patient's body). External medical devices can include ambulatory medical devices that are, for example, capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, mobile telemetry devices, and other similar wearable medical devices.

The wearable medical device can be capable of continuous use by the patient. In some implementations, the continuous use can be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. For example, the wearable medical device can be configured to be worn by a patient for as many as 24 hours a day. In some implementations, the patient may remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, heart vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, lung vibrations (e.g., using microphones and/or accelerometers positioned over the patient's thoracic area), breath vibrations, sleep related parameters (e.g., snoring, sleep apnea), tissue fluids (e.g., using radiofrequency transmitters and sensors), among others. For example, a vibrational analysis of vibrations detected via a thoracic vibrations sensor can provide information about characteristic vibrational patterns. The vibrational analysis includes monitoring for vibrations ranging from 1/10th to about 1 Hz for monitoring low frequency thoracic cavity movements such as breathing, chest wall movements, and, in some cases, heart wall movements. For example, where the sensor is substantially aligned with an apex of a ventricle of the patient, the sensor implementing vibrational analysis can detect and monitor ventricular wall motion. Similarly, other vibrational patterns can be monitored. Certain lung vibrations have characteristic patterns at various frequencies including at around 100-5000 Hz (e.g., tracheal vibrations), >500 Hz (e.g., stridor), >100-5000 Hz (e.g., wheezing), −150 Hz (e.g., rhonchus), and <350 Hz (e.g., pleural friction). Frequencies involving heart vibrations and murmurs are typically in a range from around 20 to 500 Hz. Low frequency heart vibrations are those where the dominant frequencies are less than around 100 Hz, such as S3, S4, and diastolic murmur of mitral stenosis. Certain murmurs have higher frequency components such as aortic regurgitation, where dominant frequencies are around 400 Hz.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the patient.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a number of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In some implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

In some implementations, an example of a therapeutic medical device can include a short-term continuous monitoring and/or neuromodulator for autonomic cardiovascular control, for example, a short-term outpatient wearable Tragus nerve stimulator. In such an example implementation of the short-term wearable neuromodulator, the electrode assembly can be attached to the patient's Tragus of their ear. One or more electrodes can be positioned to and configured to activate afferent branch of the patient's Vagus nerve and, potentially, other sensory nerves in that region.

In some implementations, the medical device may be a patient monitoring device with no treatment or therapy functions. For example, such a patient monitoring device can include a cardiac monitoring device or a cardiac monitor that is configured to monitor one or more cardiac physiological parameters of a patient, e.g., for remotely monitoring and/or diagnosing a condition of the patient. For example, such cardiac physiological parameters may include a patient's ECG information, heart vibrations (e.g., using accelerometers or microphones), and other related cardiac information. A cardiac monitoring device is a portable device that the patient can carry around as he or she goes about their daily routine. The cardiac monitor may be configured to detect the patient's ECG through a number of cardiac sensing electrodes. For example, a cardiac monitor may be attached to a patient via at least three adhesive cardiac sensing electrodes disposed about the patient's torso. Such cardiac monitors are used in mobile cardiac telemetry (MCT) and/or continuous cardiac event monitoring applications, e.g., in patient populations reporting irregular cardiac symptoms and/or conditions. Example cardiac conditions can include atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. For example, such patients may be prescribed a cardiac monitor for an extended period of time, e.g., 10 to 30 days, or more. In some mobile cardiac telemetry applications, a portable cardiac monitor can be configured to substantially continuously monitor the patient for a cardiac anomaly, and when such an anomaly is detected, the monitor may automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitor is configured to allow the patient to manually press a button on the cardiac monitor to report a symptom. For example, a patient may report symptoms such as a skipped beat, shortness of breath, light headedness, racing heart rate, fatigue, fainting, chest discomfort, weakness, dizziness, and/or giddiness. The cardiac monitor can record predetermined physiologic parameters of the patient (e.g., ECG information) for a predetermined amount of time (e.g., 1-30 minutes before and 1-30 minutes after a reported symptom). The cardiac monitor can be configured to monitor physiologic parameters of the patient other than cardiac related parameters. For example, the cardiac monitor can be configured to monitor, for example, heart vibrations (e.g., using accelerometers or microphones), lung vibrations, breath vibrations, sleep related parameters (e.g., snoring, sleep apnea), tissue fluids, among others.

An example process for monitoring functioning of a patient's heart using a wearable medical device is described in relation to FIG. 6 below. The at least two skin-facing electrodes 220a-b can be configured to detect one or more cardiac signals. Examples of such signals include ECG signals and/or other sensed cardiac physiological signals from the patient. The touch electrode 230 is configured to provide options for acquiring additional leads/vectors when contacted with one or more portions of one or more arms of the patient. For example, when a finger from a right hand is placed on the touch electrode 230, 232 an additional lead/vector can be formed to detect one or more cardiac signals. In an example, the additional leads/vectors may be a larger vector (e.g., no angular separation from existing continuous ECG lead/vector, but instead separation of electrodes on same lead/vector). In another example, the additional leads/vectors may be separated by at least 15° from a corresponding first one or more ECG leads in a vector cardiogram representation of the first one or more ECG leads and the second one or more ECG leads.

In certain implementations, the second one or more ECG leads provides different ECG signal characteristics relative to the first one or more ECG leads. For example, the second one or more ECG leads is configured to provide one or more of better R-wave characteristics of the ECG signal, lower signal artifacts, and better heart rate detection characteristics relative to the first one or more ECG leads. For example, better R-wave characteristics can include a higher amplitude of the R-wave in the second one or more ECG leads than the first one or more ECG leads. In an example, the second one or more ECG leads can be configured to provide better P-wave characteristics of the ECG signal relative to the first one or more ECG leads. For example, better P-wave characteristics can include a higher amplitude of the P-wave in the second one or more ECG leads than the first one or more ECG leads. For example, consider a patch implementation where the two skin-facing ECG electrodes are closely located within a same quadrant of the body of the patient. In such an example, at least one of the at least two skin-facing ECG electrodes can be located within a left lower thoracic quadrant of the patient. As noted herein in connection with FIGS. 4A-B, the left lower thoracic quadrant of the patient runs from the middle axillary line to the anterior (midsternal) median line and below the xiphoid process. In another example, at least one of the at least two skin-facing ECG electrodes can be located within a left upper thoracic quadrant of the patient. The left upper thoracic quadrant of the patient runs from the middle axillary line to the anterior (midsternal) median line and above the xiphoid process. In both such implementations, the second ECG lead that is generated when the patient touches the touch electrode can be configured to be within 15° of standard lead II in accordance with a standardized 3-lead ECG.

As the P-wave indicates atrial depolarization and occurs when the sinus node creates an action potential that depolarizes the atria, the P-wave morphology can reveal right or left atrial hypertrophy or atrial arrhythmias and can be determined via the second ECG lead. Such a P-wave may not be detected via the first one or more ECG leads, or if present may have a low magnitude such it is not easily discernable relative to noise. The characteristics of a better quality P-wave that may be detected via the second ECG lead can be based on one or more of the following criteria:

a maximal height of the P-wave being around 2.5 mm (e.g., in a range of between around 1.8 to around 3.2 mm), the direction of the wave being positive, and the P-wave duration being shorter than around 0.12 seconds (e.g., in a range of between 0.04 to 0.12 seconds).

Figure 2B:
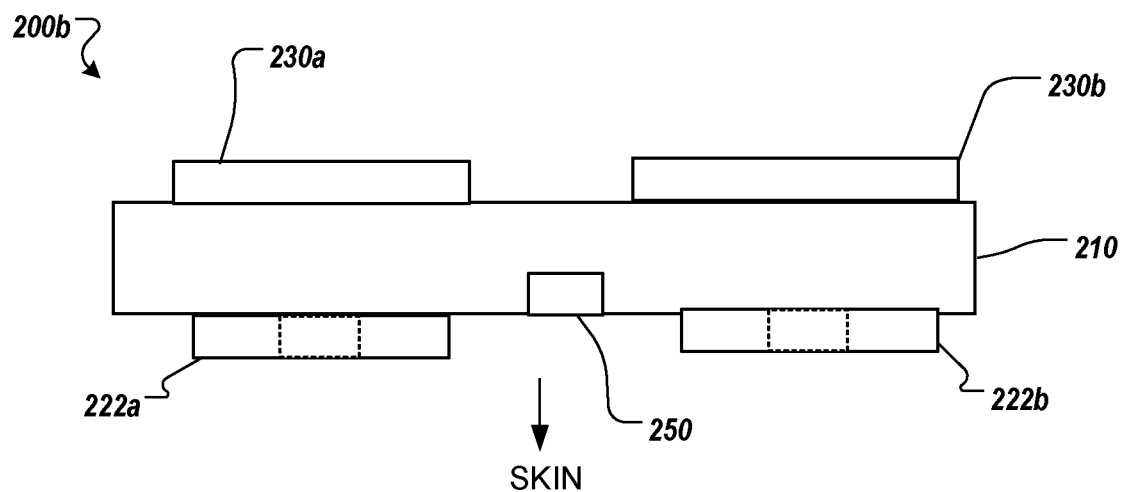

As shown in FIG. 2B, in some implementations, two touch electrodes 230a-b are disposed on the second side of the substrate 210 and configured to be contacted with one or more portions of one or more arms of the patient. In an example, each touch electrode 230a-b can be configured to be contacted with a finger of the right or left arm of the patient. The two touch electrodes 230a-b, in one illustration are configured to be contacted with a left finger of the left arm of the patient and a right finger of the right arm of the patient respectively. In an example, each touch electrode 230a-b, 232 is configured to form an additional lead/vector that is either a larger vector and/or separated by at least 15° from a corresponding first one or more ECG leads and second lead/vector in a vector cardiogram representation of the first one or more ECG leads and the second one or more ECG leads.

In some implementations, the substrate 210 can have an ergonomic shape to avoid fatigue/discomfort in prolonged maintenance of finger against electrode. In an example, a thumb grip shape can be incorporated on an edge of the substrate 210 such that an index finger can be gently placed on either touch electrode 230a-b. For example, in looking at FIG. 2A, a side portion of the substrate 210 (e.g., extending outward from the skin of the patient between electrodes 220 and touch electrode 230) may be ergonomically curved to allow for a grip indentation. In another example, the side portion of the substrate 210 may include a friction-enhanced grip region designed to encourage contact with the patient's thumb while a finger is placed on the touch electrode 230. The thumb, for example, may be aligned beside the electrode 230 (e.g., substantially where the label for substrate 210 is pointing). In another example, the thumb may align "over" the touch electrode 230 when the medical device 200 is donned by a patient.

In some implementations, the medical device 200b includes a transducer 250 for obtaining additional signals regarding heart functionality. In an example, the transducer 250 can have acoustic transducer utility and configured to monitor heart and/or lung vibrations. In an example, the acoustic transducer utility and/or the transducer 250 can be configured to detect heart vibration values including any one or all of S1, S2, S3, S4, and murmurs. From these heart vibration values, certain heart vibration metrics may be calculated, including any one or more of electromechanical activation time (EMAT), percentage of EMAT (% EMAT), systolic dysfunction index (SDI), left ventricular diastolic perfusion time (LDPT), and left ventricular systolic time (LVST). Certain heart vibration metrics can be used to determine patterns and thresholds (e.g., S3 more pronounced over time).

The transducer 250, in some implementations, is configured to collect data on heart rate, respiration rate, activity, and posture, all of which are analyzed using the at least one processor to determine patient-specific vital signs trends. In an example, the transducer 250 can have radio frequency (RF) transducer utility and be configured to detect a change in an amount of fluid in the patient's lungs and chest cavity. In another example, the transducer 250 can have accelerometer utility configured to detect a respiration rate, snoring, and sleep apnea. In a further example, the transducer 250 can be an acoustic transducer in communication with the at least one processor and configured to detect one or more vibrations of the patient.

Figure 2C:
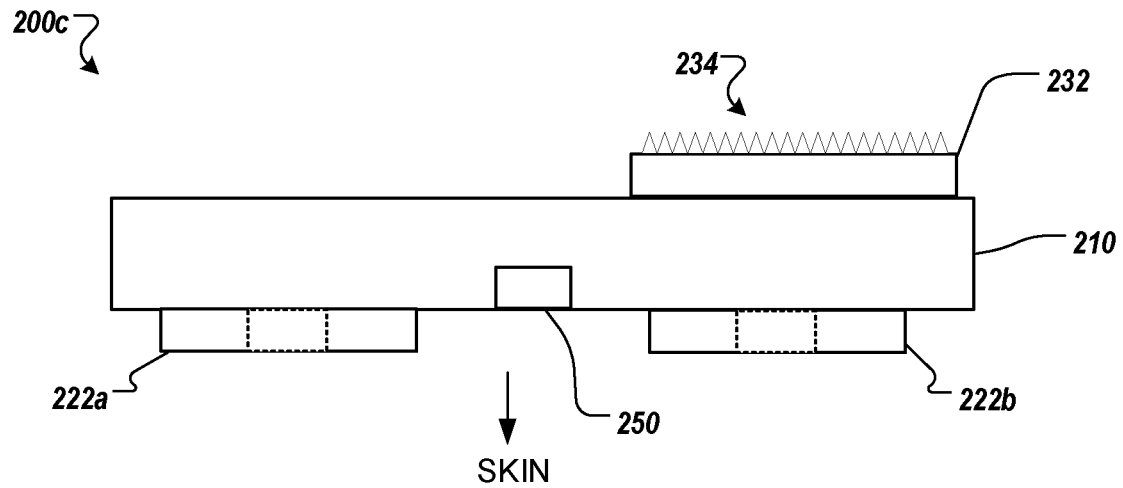
FIGS. 2C and 2D depict example wearable medical devices similar to those of FIGS. 2A and 2B, including a projection mechanism for obtaining a more consistent signal from the finger placement.

As shown in FIG. 2C, in some implementations, a medical device 200c includes a substrate 210c having at least two adhesive ECG electrodes 222a-b, which can be disposed on a first side of the substrate 210c and configured to be in continuous contact with skin of the patient as well as one or more touch electrodes 232 having a number of projections or barbs 234 adapted to at least partially penetrate an epidermis of the skin/finger of the patient. The projections 234, for example, may be configured for obtaining a more consistent signal from the finger placement through maintaining constant contact at least via the projections 234. Further, the projections 234 may supply a tactile feedback to the patient (e.g., akin to touching sandpaper) to ensure the patient's proper contact with the touch electrode 232. The projections 234, in some embodiments, are integrated into the touch electrode design. In other embodiments, the projections 234 are incorporated into a replaceable strip configured for insertion against an upper surface of each touch electrode 232. Optionally, the projections 234 can be configured to penetrate a deeper layer of skin than the epidermis of the skin/finger of the patient. With deeper penetration, for example, the signal may be enhanced through ensuring a moister contact than the epidermis may supply. However, deeper contact may cause some patient discomfort.

Figure 2D:
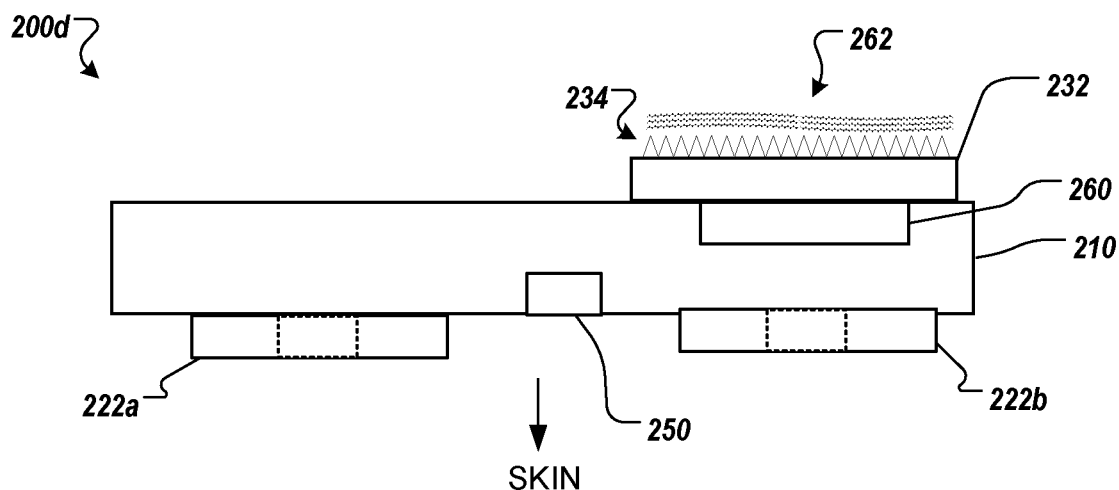

As shown in FIG. 2D, in some implementations, a medical device 200d includes a substrate 210d having at least two ECG electrodes 222a-b disposed on a first side of the substrate 210d and configured to be in continuous contact with skin of the patient, one or more touch electrodes 232 having a number of projections 234 adapted to at least partially penetrate an epidermis of the skin/finger of the patient, a transducer 250 for obtaining additional signals regarding heart functionality, and at least one vibrating element 260 (e.g., piezoelectric vibrator unit) configured to cause a vibration 262 towards each of the one or more touch electrodes 232. In some embodiments, the vibrating element 260 is configured to cause a vibration 262 providing the patient with tactile feedback. For example, the vibrating element 260 may be configured to issue the vibration 262 upon sensing (e.g., via detection of an additional touch sensor enabled lead by the processor or via a separate sensing element such as a pressure sensor) placement of a portion of the patient's arm upon the touch electrode 232 to assure the patient of appropriate contact and to encourage continued placement. In some embodiments, the vibrating element 260 is configured to generate the vibration 262 in order to enhance penetration of the epidermis of the skin/finger of the patient by the projections 234.

Figure 2E:
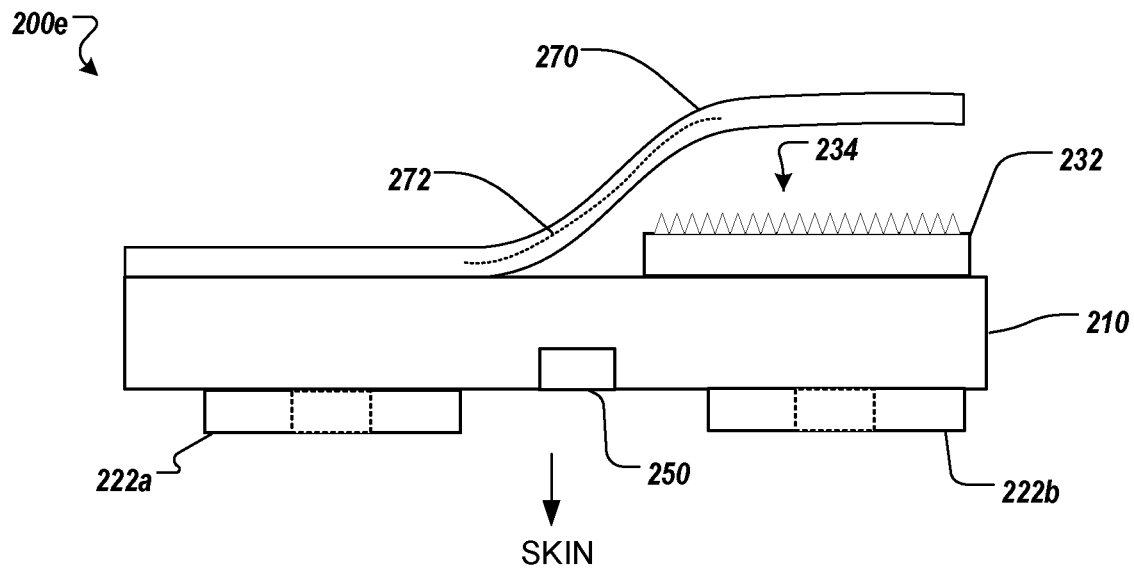
FIGS. 2E and 2F depict example wearable medical devices similar to those of FIGS. 2A through 2D, including means for maintaining a patient's finger against the device.

In some cases, the patient may fail to maintain proper finger placement on the one or more touch electrodes 230, 232 due to patient fatigue or movement, resulting in inconsistent signal. As shown in FIG. 2E, in some implementations, a medical device 200e such as one of the medical devices 200a-d further includes a housing 270 to aid in maintaining finger position. The housing 270, in some embodiments, is a flexible cuff or cover designed to be flush with substrate 210 when not used. The cuff or cover, for example, may be designed to accept at least a portion of the fingertip of the patient, for example abutting at least one of a tip and a side of the fingertip as well as an upper surface of the fingernail. In a particular illustration, the flexible cuff may be designed to surround the fingertip. In some embodiments, the housing 270 includes a flexible spine element 272 configured to flex away from the substrate 210 upon insertion of a fingertip, providing adequate space for positioning while asserting gentle pressure against the fingertip to maintain positioning. The flexible spine element, for example, may be designed to abut a fingertip or side of the finger of the patient.

Figure 2F:
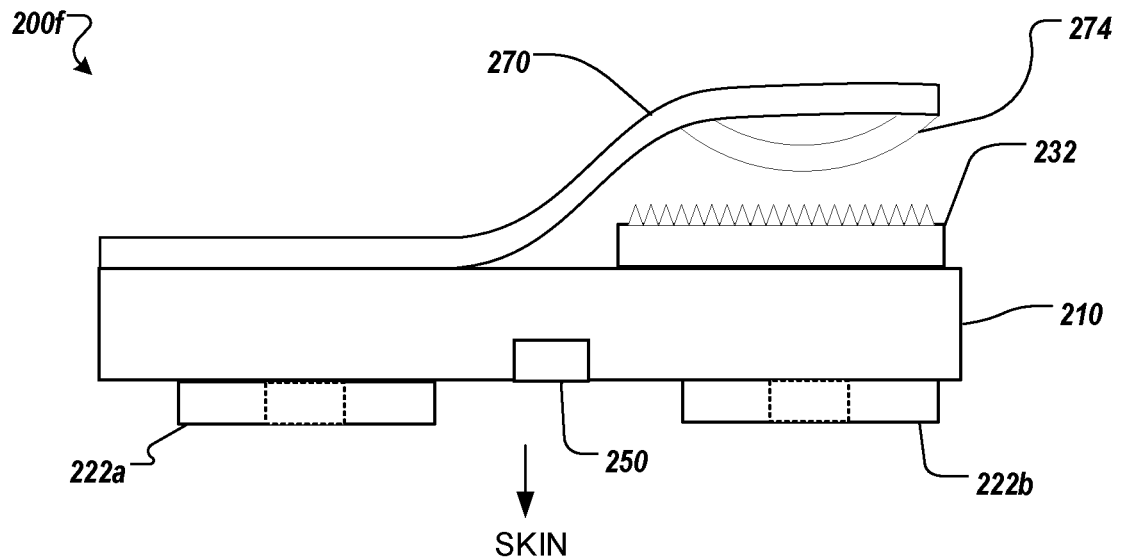

As shown in FIG. 2F, in some implementations, the housing 270 further includes one or more securing elements 274 for exerting downward pressure toward the touch electrode 232. The securing element(s) 274, in some examples, can include an air bladder, leaf spring, or spring hinge. In other implementations, rather than exerting pressure, the securing element(s) 274 includes friction-enhancing material, such as a rubberized or textured surface, to maintain position of the portion of the finger of the patient.

Other options are possible in encouraging proper finger placement and contact maintenance. In an example, the housing 270 can further include a tether linking a touch sensor with the touch electrode 232 such that, to avoid fatigue/discomfort in prolonged maintenance of finger against touch electrode 232. The patient may instead maintain contact with the housing while the housing is disposed in a more comfortable position, such as upon a lap or against a shoulder of the patient. In some embodiments, the medical device 200 provides feedback that finger properly positioned, such as the feedback discussed in relation to the vibrating element 260 of FIG. 2D. In addition to or instead of vibration, in some examples, upon detection of proper placement visual or audible feedback may be supplied to the user. The feedback, in some examples, may be provided via one or more LED elements, a speaker, or a transducer. Alternatively, upon detection of failure to maintain appropriate contact, visual or audible feedback may be introduced (e.g., blinking lights, beeping, etc.) to encourage the patient to more securely position the finger, hand, or arm against the touch electrode. In a particular example, a controller may provide verbal instruction to the patient via a speaker element.

Example Triggering Scenarios

In some implementations, the patient is prompted to place a portion of an arm on one or more touch electrodes 230, 232 of the medical device 200. In an example, the patient can be prompted to place a finger against one of the touch electrodes 230, 232 or to insert a finger in the housing 270. The prompting, for example, can be provided by the controller (e.g., through verbal instruction to the patient). In another example, the prompting may be supplied through a portable computing device application such as a smart phone app designed to supply prompts to the user to obtain data. The prompts, in one example, are intermittent throughout the day (e.g., scheduled on a periodic basis, such as every 6 hours). In another example, the prompts may be supplied to the user upon detection of an irregularity in continuously monitored patient data, such as ECG data, respiratory data, heart rate data, or other bioinformation. For example, the controller, upon detection of a threshold difference between monitored data and acceptable health metrics may trigger prompting of the patient.

The medical device can include an output device (e.g., speaker, alarm) configured to output a notification to the patient. In some embodiments, the medical device 200 is configured to monitor cardiac data and to produce an alarm or notification for the patient to touch the one or more touch electrodes 230, 232 in order to obtain additional ECG data upon identifying threshold differences between data metric values and acceptable (or typical) data metric values. In some implementations, data metric values can be based on signal quality issues, patient activity, and clinical indications. Examples of signal quality issues include noisy ECG signals on the skin-facing electrodes and/or the touch electrodes. In illustration, upon noisiness exceeding a threshold level, the patient may be notified to contact one or more touch electrodes 230,232. A user-defined threshold of noise and/or frequency of noisy events, for example indicated by a medical professional, may be used in determining an acceptable data metric value. Examples of patient activity can include motion sensor detection of recent strenuous activity performed by the patient, geolocation information identifying a patient leaving the gym, or data values logged from other devices indicating increased activity level (e.g., an exercise monitor identifying a period of increased activity). Examples of clinical indications include sensor detection of a predetermined arrhythmia event, for example, where bradycardia or tachycardia onset/offset is detected or where an arrhythmia event is sustained for a threshold period of time such as greater than 1 minute. Threshold differences and/or lengths of clinical indication events may be user-specified such that a medical professional may adjust thresholds based upon the particular patient. In any of the above cases involving threshold differences between data metric values and acceptable/typical data metric values, the medical device 200 can trigger the notification for the patient to contact one or more touch electrodes 230, 232 for additional ECG data.

In some implementations, data metric values can differ depending on a placement of the medical device 200 on the patient. In an example, the vibrations sensor can detect pleural effusion in a lung of the patient and produce the alert or notification, where the threshold for acceptable data metric values varies based on positioning of the medical device 200 on the chest of the patient. In an example, the vibration sensor can sense symptoms of progressing pleural effusion including frequency of coughing, difficulty breathing when lying down, shortness of breath, difficulty taking deep breaths, persistent hiccups, respiratory rate with and without activity, etc.

Additional clinical triggers for requesting that the patient place finger on touch electrode include criterion for known cardiac conditions such as Bradycardia and Tachycardia. In some implementations, when the patient's average heart rate drops below a predetermined threshold, the medical device 200 may determine that the patient has entered Bradycardia and request that the patient contact a touch electrode to collect additional ECG data. The heart beats, for example, may be counted based upon radio-frequency or vibration sensor output. In other embodiments, the heart beat information may be collected through a separate heart monitoring device, such as a portable health monitor, in communication with the medical device. Detection, in some examples, may be performed by analyzing at least twenty heart beats or a series of heart beats over a period of at least thirty seconds. The threshold, for example, may be in a range from 20 to 60 beats per minute. In an illustrative example, the threshold may be user-configurable (e.g., by a medical professional) within a range of 20 to 60 beats, with 40 being a default value.

Further, in some implementations, when the patient has been determined by the medical device to be expressing Bradycardia and the patient's average heart rate rises above a predetermined threshold (e.g., established as discussed above), the medical device 200 may determine that the patient has exited Bradycardia and may request that the patient contact one or more touch electrodes to collect additional ECG data. In some embodiments, the threshold for determining the patient has exited Bradycardia may differ from the threshold for determining the patient has entered Bradycardia. For example, while the default value illustrated above was 40 beats per minute, the threshold for exiting Bradycardia may be set to 45 beats per minute. The threshold for exiting, as with the threshold for entering, may be configurable by a medical professional. Conversely, the threshold for exiting may be automatically configured to match or exceed the threshold for entering. For example, the threshold for exiting may default to 5 bpm greater than the threshold for entering.

In some implementations, when the patient's average heart rate rises above a second, different predetermined value, the medical device 200 may determine that the patient has entered Tachycardia and request that the patient place finger on the touch electrode to collect additional ECG data. The heart beats, for example, may be counted based upon radio-frequency or vibration sensor output. In other embodiments, the heart beat information may be collected through a separate heart monitoring device, such as a portable health monitor, in communication with the medical device. Detection, in some examples, may be performed by analyzing at least twenty heart beats or a series of heart beats over a period of at least thirty seconds. The threshold, for example, may be in a range from 100 to 250 beats per minute. In an illustrative example, the threshold may be user-configurable (e.g., by a medical professional) within a range of 100 to 250 beats, with 110 bpm being a default value.

Further, in some implementations, when the patient has been determined by the medical device 200 to be expressing Tachycardia and the patient's average heart rate lowers below a predetermined threshold (e.g., established as discussed above), the medical device 200 may determine that the patient has exited Tachycardia and may request that the patient contact one or more touch electrodes to collect additional ECG data. In some embodiments, the threshold for determining the patient has exited Tachycardia may differ from the threshold for determining the patient has entered Tachycardia. For example, while the default value illustrated above was 110 beats per minute, the threshold for exiting Bradycardia may be set to 100 beats per minute. The threshold for exiting, as with the threshold for entering, may be configurable by a medical professional. Conversely, the threshold for exiting may be automatically configured to be equal or lower than the threshold for entering. For example, the threshold for exiting may default to 10 bpm less than the threshold for entering.

In an example, the at least one processor can be configured to apply basic metrics to irregularity index/indices and initiate the alarm and notification when the ECG data is beyond a certain threshold. In an example, the at least one processor can be configured to apply thresholds of probability prior to producing an alarm and notification. Thresholds may be set based in part on sensor data from the at least two skin-facing electrodes 220a-b. The thresholds, further, may be based in part on additional patient data metrics. Thresholds may be adjusted based upon patient demographics or other patient information. For example, the thresholds may be customized on per-patient basis (e.g., stored in cloud or on the memory of the medical device) to consider one or more of patient demographics (e.g., age, sex, weight, height, etc.), current medications, past health history, diagnosed medical conditions, baseline ECG readings, and/or other baseline health metrics. In an example, the at least one processor can be configured to generate probability on sliding scale.

In certain implementations, the medical device is configured to receive additional sensor/patient data from a remote computing device. In an example, patient specific data may be available on a local computing device in communication with the medical device, such as a portable computing device or recharging/communication system designed to operate with the medical device. In another example, the patient specific data may be supplied from a remote computing device, such as a cloud-based server system directly or indirectly in communication with the medical device. For example, the medical device may be placed in communication with the cloud-based server system via another local computing device such as a portable smart device or a recharging/communication system. Further, one or more additional sensor(s) external to wearable medical device (e.g., integrated into modular garment as in FIG. 5, integrated in another portable health monitoring system carried or worn by the patient, etc.) may supply at least a portion of the patient specific data. The patient specific data, for example, may be provided to the medical device from the additional sensor(s) directly via a wireless communications system, or indirectly through interfacing with an intermediate system such as a portable computing device or recharging/communication system. In some examples, the patient specific data can include age, BMI, known diseases or disorders, and/or current medications. The patient specific data, in further examples, can include baseline data such as resting heart rate or resting respiration.

Each modality of detection, in some embodiments, may correspond to a different irregularity index. For example, the at least two skin-facing electrodes 220/222 can be configured to detect a change in ECG signal pattern frequency (e.g., FFT), power, amplitude, phase, and rate of change, RR variability, low heart rate (under 40), escalated heart rate (over 140). In an example, the transducer 250 may be an RF transducer configured to detect a change in an amount of fluid in the patient's lungs and chest cavity. The transducer 250, in another example, includes an accelerometer configured to detect a respiration rate that is ramping up/down or above/below a respiration threshold (e.g., over 15 breaths/min, under 8 breaths/min). In a further example, the transducer 250 includes an acoustic transducer configured to detect one or more vibrations of the patient (e.g., S3 more pronounced over time, distance between r-wave peak and valve closure). In certain implementations, the irregularity index can be based on a calculation of an event estimation of risk score associated with a potential medical event for a patient as described in U.S. publication US20160135706A1, titled "Medical Premonitory Event Estimation" herein incorporated in its entirety. In certain implementations, the medical device is configured to generate irregularity index/indices based on combining the heart vibration metrics and the ECG data.

In certain implementations, the medical device 200 includes communications circuitry for receiving instructions from a remote computing system and for transmitting the ECG data to the remote computing system. In an example, the medical device 200 can be configured to substantially continuously monitor the patient for a cardiac anomaly and, when such an anomaly is detected, the medical device may automatically send data relating to the anomaly to the remote computing system. Based on a determination by the remote computing system, the medical device 200 can receive a command from the remote computing system requesting additional ECG data. The medical device can be configured to produce a prompt such as a verbal prompt or an alarm notifying the patient to touch the one or more touch electrodes 230, 232 in order to obtain additional ECG data.

An example process for analyzing signals obtained from electrodes of a wearable medical device is described in FIGS. 7A and 7B below.

In certain implementations, the patient initiates monitoring through proactive touching of the touch electrode(s) 230, 232. For example, the patient may be instructed to place a portion of an arm on the electrode(s) 230, 232 periodically throughout the day and/or when experiencing onset of one or more symptoms (e.g., heart racing, light-headedness, fatigue, etc.). Further to the example, the at least one processor may be configured to wait for a minimum period of time (e.g., ~3 seconds) upon an initial contact of the touch electrode(s) 230, 232 before ECG recording is initiated. This wait can prevent accidental touches from activating needless recording and battery drain. In certain implementations, the at least one processor is configured to buffer a minimum period of time (e.g., ~3 seconds) upon an initial contact of the touch electrode(s) 230, 232 before ECG recording is used for diagnosis or saved to memory. The buffered ECG recording can prevent inadvertent activation.

In certain implementations, the medical device 200 identifies contact with the touch electrode(s) 230, 232 indicative of patient-elected monitoring. The medical device 200 can determine that a portion of the patient is touching the one or more touch electrodes 230, 232 in several ways. In an example, the at least one processor can be configured to "wake up" periodically (e.g., ~1 sec) to check for an impedance change at the one or more touch electrodes 230, 232. In an example, the one or more touch electrodes 230 can be touch sensitive to sense a touch and "wake up" the at least one processor. In an example, the one or more touch electrodes 230 can function as a button that triggers the at least one processor.

In certain implementations, a voice-initiated user interface command is provided to wake up the controller and initiate interaction with the patient. In an example, the at least one processor may be configured to detect when one of the touch electrodes 230, 232 is contacted with one or more portions of one or more arms of the patient and to cause the output device to output a message to the patient. For example, the message may be a query supplied by a voice-initiated user interface (e.g., similar to Siri™ by Apple, Inc. of Cupertino, CA) such as "Patient, would you like to record a new ECG recording?" and "Patient, if you would like to record a new ECG recording, please continue to touch the electrode until recording is complete." The message, for example may supply feedback to the patient on positioning of the patient touching the touch electrode and a timing for holding their skin to the touch electrode. In an illustration, the message can instruct the patient to select a particular arm (e.g., left vs. right) for holding their skin to the touch electrode. The timing can include a countdown with audible and/or visual feedback. In some embodiments, based upon failure of response to patient prompts, the user interface may gradually modify in urgency and/or intensity. For example, the user interface can modify a tone, and/or light display in volume, frequency, and/or shrillness to regain the patient's attention. Further, the user interface may supply a shrill signal and/or special verbal command sequence when the patient is presumed unconscious due to a threshold period of unresponsiveness.

FIGS. 4A and 4B depict example positioning and anatomical locations of placement of the wearable medical device 200 and example electrode placements for obtaining metrics regarding the functioning of the patient's heart. In an example, at least one of the at least two skin-facing ECG electrodes can be located within a left lower thoracic quadrant of the patient, while the second ECG lead is within 15° of standard lead II in accordance with a standardized 3-lead ECG. The left lower thoracic quadrant of the patient runs from the middle axillary line (412) to the anterior (midsternal) median line (404) and below the xiphoid process (416). In an example, at least one of the at least two skin-facing ECG electrodes can be located within a left upper thoracic quadrant of the patient, while the second ECG lead is within 15° of standard lead II in accordance with a standardized 3-lead ECG. The left upper thoracic quadrant of the patient runs from the middle axillary line (412) to the anterior (midsternal) median line (404) and above the xiphoid process (416).

In an example, one or more of the at least two skin-facing ECG electrodes can be located on either anterior or lateral thorax locations of the patient, which can be considered as below the sternum/jugular notch (406) and above the xiphoid process (416). In an example, the at least two skin-facing ECG electrodes can be located on one or more of a left mid-clavicular region, a left mid-axillary region, a right mid-clavicular region, and a right mid-axillary region of the patient. The mid-axillary region is given as to be over the rib cage, between the posterior axillary line (414) and the anterior axillary line (410). The mid-clavicular region is given as below the sternum/jugular notch (406) and from the anterior axillary line (410) to the anterior (midsternal) median line (404).

In certain implementations, the one or more touch electrodes 230 can be configured to enhance detection of atrial depolarization of the heart (e.g., P-wave in standard lead I). In an example, at least one of the two skin-facing ECG electrodes is configured to be in line with the sternal clavicular junction (422) and midpoint of the left costal margin in line with the seventh intercostal space (424) as shown at by the dotted line 420 in FIG. 4C.

In certain implementations, an adhesive-based medical dressing material, such as adhesive Tegaderm™ from 3M Company (Maplewood, Minnesota), can be applied over medical device 200 to secure the medical device 200 to the skin of the patient. Such material may be breathable material, e.g., material that allows moisture vapor to evaporate from the skin and/or is permeable to oxygen.

Figure 3C:
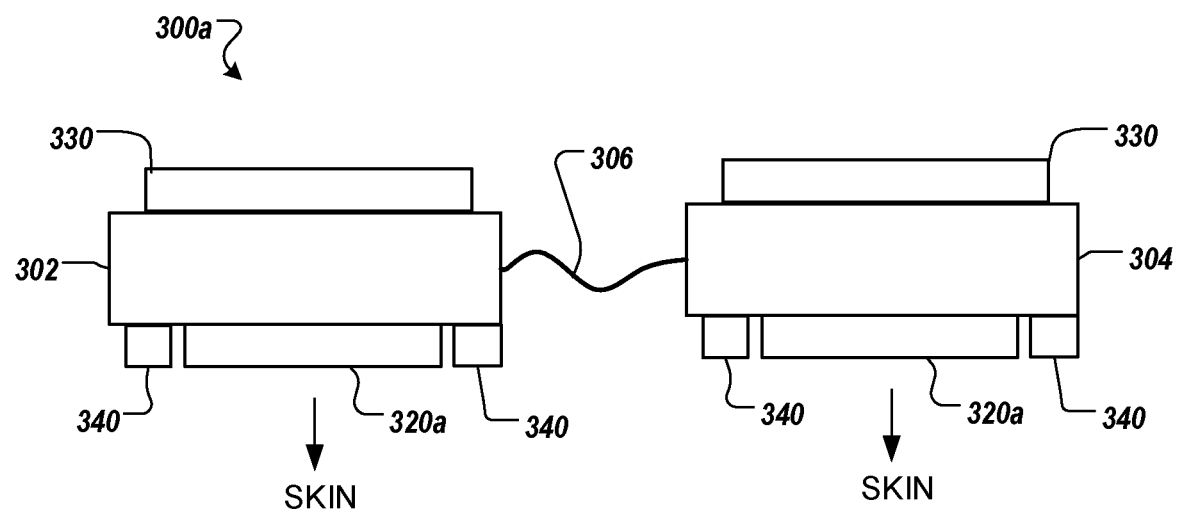
FIG. 3C depicts a side view of the wearable medical device shown in FIG. 3A according to an example.

FIGS. 3A-C illustrate examples of a wearable medical device 300a-b that is external, ambulatory, and wearable by a patient, and configured to implement one or more processes described herein. In certain implementations, the medical device 300a can include a number of ECG electrodes disposed in spaced apart positions about a torso of a patient and configured to be in continuous contact with skin of the patient, one or more touch electrodes configured to be contacted with one or more portions of one or more arms of the patient, ECG circuitry in communication with the ECG electrodes and the one or more touch electrodes. Adhesive can be connected to each electrode. Alternatively, an adhesive-based medical dressing material can be applied over each electrode to secure the electrode to the skin of the patient.

In the implementations illustrated in FIGS. 3A through 3C, at least one of the ECG electrodes is disposed above the heart and least one of the ECG electrodes at least in spaced apart positions about torso of a patient.

Referring to FIG. 4C, alternatively, the electrodes may be placed such that they are configured to be substantially inline with the dotted line 420 defined by sternal clavicular junction (422) and the midpoint of the left costal margin inline with the seventh intercostal space (424), for instance, approximately equidistant from 422 and 424 along the dotted line 420. Such a location, for example, may provide a non-standard ECG vector using non-standard ECG electrode locations, and where the vector angle difference is approximately orthogonal. The orthogonal vector angle difference may be diagnostically beneficial since there is more independent information in the two ECG leads about the electrical activity of the heart.

In some embodiments, one of the electrodes may be placed on the neck, or on the ear adjacent to the tragus nerve. To enable the electrode to also be used as a stimulation electrode for tragus or vagal nerve stimulation.

The medical device 300a-b can include one or more of the following: a first substrate 302, a second substrate 304, multiple ECG electrodes 320, one or more touch electrodes 330, 332 (optionally having a number of projections and/or a housing to aid in maintaining finger position as described in relation to FIGS. 2E-F), ECG circuitry, a memory, at least one processor, an antenna, a patient interface, a transducer (e.g., transducer 250 described in relation to FIGS. 2B-2F), a vibrating element (e.g., element 260 as described in relation to FIG. 2D), a battery or any combination of these. In certain embodiments, at least some of the components of the medical device 300a-b are configured to be affixed to the substrate 302, 304 while others may be permanently integrated into the substrate 302, 304. Each of the substrates 302, 304 may be configured for releasably mounting to a patient's chest.

As shown in FIGS. 3A and 3C, in certain implementations, the medical device 300a includes the first substrate 302 having at least one ECG electrode 320 disposed on a first side of the first substrate and configured to be in continuous contact with skin of the patient and a second substrate 304, in communication with the first substrate 302, having at least one ECG electrode 320 disposed on a first side of the second substrate 304 and configured to be in continuous contact with skin of the patient. The medical device 300a further includes one or more touch electrodes 330 disposed on a second side of at least one of the first substrate 302 and the second substrate 304 and configured to be contacted with one or more portions of one or more arms of the patient. In some implementations, the second substrate 304 is in communication with the first substrate 302 with wiring 306. For example, one of the substrates 302, 304 may include the "brains" (e.g., processing circuitry and/or communication circuitry while the signals of the electrodes 320, 330 of the other substrate 302, 304 are transmitted via the wiring 306 to the "brains" for handling. In some implementations, a first substrate 302, 304 can include a signal processor configured to amplify, filter, and digitize these cardiac signals prior to transmitting the cardiac signals to the ECG circuitry of a second substrate 302, 304.

As shown in FIG. 3B, in some implementations, rather than having the first substrate 320 in direct communication with the second substrate 330, the medical device 300b includes a central controller 308 in communication with the first substrate 302 and the second substrate 304 using wiring 306. The central controller, for example, may include at least a portion of the ECG circuitry, a memory, at least one processor, an antenna, a patient interface, and a battery within a housing. Further, the central controller 308 can include one or more of the following components of the medical device 300a-b: one or more ECG electrodes 320, one or more touch electrodes 330 (optionally having a number of projections and/or a housing to aid in maintaining finger position as described in relation to FIGS. 2E-F), a transducer (e.g., transducer 250 described in relation to FIGS. 2B-2F), and a vibrating element (e.g., element 260 as described in relation to FIG. 2D). For example, in positioning at least one touch electrode 330 on the central controller 308, the patient may be able to readily and comfortably reach the touch electrode 330 rather than needing to reach beneath clothing. For example, the central controller 308 may be worn on a belt or otherwise secured around the waist of the patient. Further, the central controller 308 may be configured to perform the user interface processes and provide patient prompts as described above in relation to FIGS. 2A-F. In some implementations, one or more of the substrates 302, 304 can include a signal processor configured to amplify, filter, and digitize these cardiac signals prior to transmitting the cardiac signals to the ECG circuitry of the central controller 308.

The medical device 300a-b, in some implementations, is configured to identify one or more non-standard ECG vectors and to determine, based on sensed ECG data, a first electrode lead/vector. For example, the at least one processor may be configured to infer a location and/or orientation of each electrode based on a ECG characteristic (e.g., lead/vector morphology). In certain implementations, any one of the first substrate 302 and the second substrate 304 can be repositioned to create a new lead/vector with the touch electrode. For example, the patient can place their finger in the housing 270 and move the substrate 302, 304 to a different position to form a larger vector and/or a different lead separated by at least 15° from a corresponding first lead/vector in a vector cardiogram representation. In an embodiment, the medical device can perform a skin conductance check with another skin-facing electrode and a touch electrode to determine the location of the substrate 302, 304.

In some implementations, the at least one processor of the medical device 300a-b or in communication with the medical device 300a-b can determine that a specific lead orientation is required that includes on one or more portions of a specific arm of the patient (e.g., a left arm or a right arm) as a portion of the circuit. For example, the at least one processor can determine that a lead is required including at least part of the patient's left arm. For example, in an implementation, the device 300a-b along with its skin-facing electrodes may be located on a left side of the patient (e.g., within a left lower thoracic quadrant as described above). In an example scenario, the processor of such a device 300a-b can determine that a better lead is needed to collect more information about P-wave characteristics of the patient's ECG. The processor may be unable to sense a P-wave signal of sufficient magnitude to discriminate the signal from surrounding signal noise. The processor may additional determine that a standard Lead II or a nonstandard lead that approximates a standard Lead II may be desirable. In such a circumstance, the processor may prompt the patient to place a finger of the left arm on the touch electrode to get an additional lead for viewing the electrical activity of the patient's heart. As previously noted, such a better P-wave that may not have been detected via the first one or more ECG leads may now be detected via the second ECG lead based on one or more of the following criteria: a maximal height of the P-wave being around 2.5 mm (e.g., in a range of between around 1.8 to around 3.2 mm), the direction of the wave being positive, and the p-wave duration being shorter than around 0.12 seconds (e.g., in a range of between 0.04 to 0.12 seconds).

In some implementations, a first substrate 302, 304 can include a magnetometer configured to detect an orientation of one or more portions of the medical device 300a-b in relation to the Earth's magnetic field. In an example, in combination with a conductance test between two or more ECG electrodes 320, the magnetometer may be used to determine an orientation of each substrate 302, 304. In another example, the magnetometer may be used to determine an orientation of each substrate 302, 304 relative to each other. In some implementations, the determined orientation of each substrate 302, 304 may be used in calculating a lead/vector.

The medical device 300*a-b*, in some implementations, is configured to aid the patient in identifying and locating the appropriate electrode configured to form the specific lead orientation. In an example, each touch electrode can be configured to provide haptic feedback to aid the patient in identifying and locating the appropriate electrode configured to form the specific lead orientation. In an example, the haptic feedback can be a Transcutaneous Electrical Nerve Stimulation (TENS) therapy delivered between two or more electrodes near one or more touch electrodes. In another example, the haptic feedback can be provided by a vibrating element (such as the vibrating element 260 of FIG. 2D) integrated with the substrate 302, 304.

Example Monitoring and Treatment Garment

Figure 5:
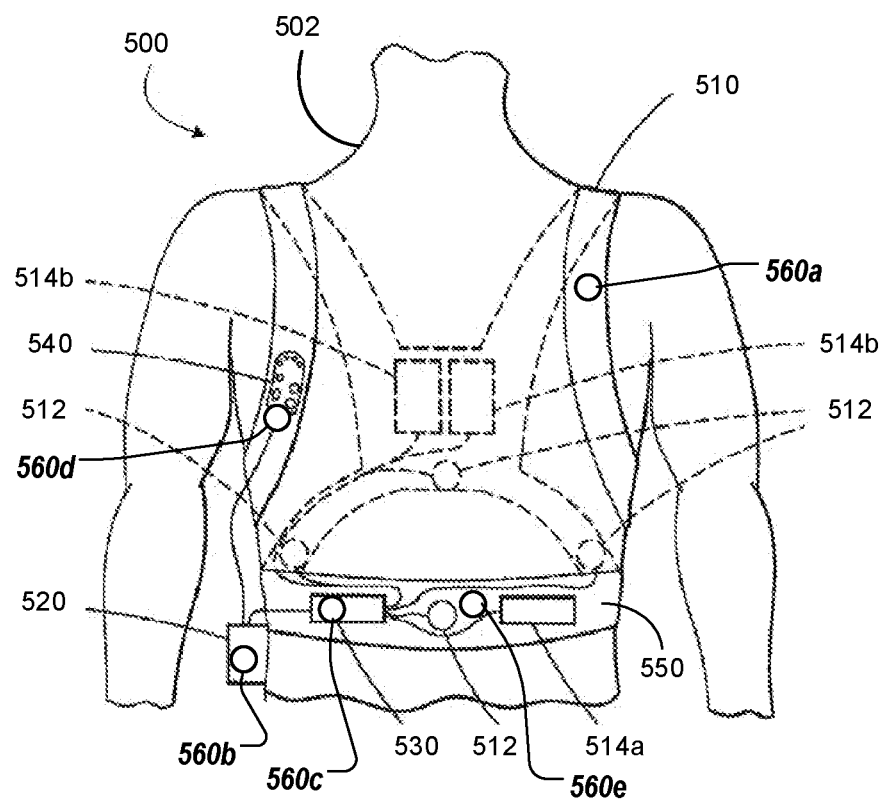
FIG. 5 depicts an example wearable medical device including a defibrillator vest.

FIG. 5 illustrates an example medical device 500 that is external, ambulatory, and wearable by a patient 502, and configured to implement one or more processes described herein. For example, the medical device 500 can be a non-invasive medical device configured to be located substantially external to the patient. Such a medical device 500 can be, for example, an ambulatory medical device that is capable of and designed for moving with the patient as the patient goes about his or her daily routine. For example, the medical device 500 as described herein can be bodily-attached to the patient such as the LifeVest® wearable cardioverter defibrillator available from ZOLL® Medical Corporation. In one example scenario, such wearable defibrillators can be worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 500 can include one or more of the following: a garment 510, multiple sensing electrodes 512 (e.g., ECG electrodes), one or more therapy electrodes 514*a* and 514*b* (collectively referred to herein as therapy electrodes 514), a medical device controller 520, a connection pod 530, a patient interface pod 540, a belt 550, ECG circuitry, one or more touch electrodes 560*a-e* or any combination of these. In some examples, at least some of the components of the medical device 500 can be configured to be affixed to the garment 510 (or in some examples, permanently integrated into the garment 510), which can be worn about the patient's torso. In an example, the one or more touch electrodes can be coupled to the garment using snaps (not shown).

The medical device controller 520 can include a memory in communication with the ECG circuitry and at least one processor in communication with the memory and the ECG circuitry. The medical device controller 520 can be operatively coupled to the sensing electrodes 512 and the one or more touch electrodes 560*a-e* via the ECG circuitry. The connection pod 530 can, in some examples, include a signal processor configured to amplify, filter, and digitize these cardiac signals prior to transmitting the cardiac signals to the ECG circuitry of the medical device controller 520.

In some embodiments, the sensing electrodes 512 and/or the touch electrode(s) 560 are affixed to the garment 510. For example, one or more of the sensing electrodes 512/and or the touch electrode(s) 560 may be assembled into the garment 510 or removably attached to the garment, such as by using hook and loop fasteners. In some implementations, the sensing electrodes 512 and the one or more touch electrodes 560*a-e* are permanently integrated into the garment 510. As illustrated, in some examples, a touch electrode 560*a-e* can be integrated into one or more of the garment 510 (touch electrode 560*a*), the medical device controller 520 (touch electrode 560*b*), the connection pod 530 (touch electrode 560*c*), the patient interface pod 540 (touch electrode 560*d*), and/or the belt 550 (touch electrode 560*e*). In another embodiment, a touch electrode can be positioned on an inner side of the garment where the garment can be used to help apply pressure to keep the patient's finger pressed against the touch electrode.

Component configurations other than those shown in FIG. 5 are possible. For example, the sensing electrodes 512 can be configured to be attached at various positions about the body of the patient 502. The sensing electrodes 512 and the one or more touch electrodes 560*a-e* can be operatively coupled to the medical device controller 520 through the connection pod 530. In some implementations, the sensing electrodes 512 and the one or more touch electrodes 560*a-e* can be adhesively attached to the patient 502. In some implementations, the sensing electrodes 512, the one or more touch electrodes 560*a-e*, and at least one of the therapy electrodes 514 can be included on a single integrated patch and adhesively applied to the patient's body.

The sensing electrodes 512 can be configured to detect one or more cardiac signals. Examples of such signals include ECG signals and/or other sensed cardiac physiological signals from the patient. Example sensing electrodes 512 include conductive electrodes (e.g., silver/silver chloride electrodes, as described further below) or dry electrodes (e.g., a metal electrode with an oxide coating such as tantalum pentoxide electrodes, as described in, for example, U.S. Pat. No. 6,253,099 entitled "Cardiac Monitoring Electrode Apparatus and Method," the content of which is incorporated herein by reference).

In certain implementations, the sensing electrodes 512 can be incorporated into sensing devices including additional components such as accelerometers, acoustic signal detecting components, and other measuring components for recording additional parameters. For example, the sensing electrodes 512 and the one or more touch electrodes 560*a-e* can be incorporated into sensing devices also configured to detect other types of patient physiological parameters and acoustic signals, such as tissue fluid levels, heart vibrations, lung vibrations, respiration vibrations, patient movement, etc.

One or more of the therapy electrodes 514, in some implementations, are configured to deliver one or more therapeutic defibrillating shocks to the body of the patient 502 when the medical device 500 determines that such treatment is warranted based on the signals detected by the sensing electrodes 512 and processed by the medical device controller 520. Example therapy electrodes 514 can include conductive metal electrodes such as stainless-steel electrodes that include, in certain implementations, one or more conductive gel deployment devices configured to deliver conductive gel to the metal electrode prior to delivery of a therapeutic shock. In some embodiments, the therapy electrodes 514 are incorporated into sensing devices including one or more additional sensors configured to detect ECG signals as well as other physiological signals of the patient.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 514 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or for a specific patient. Alternatively, the optional therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Example Processes

Figure 6:
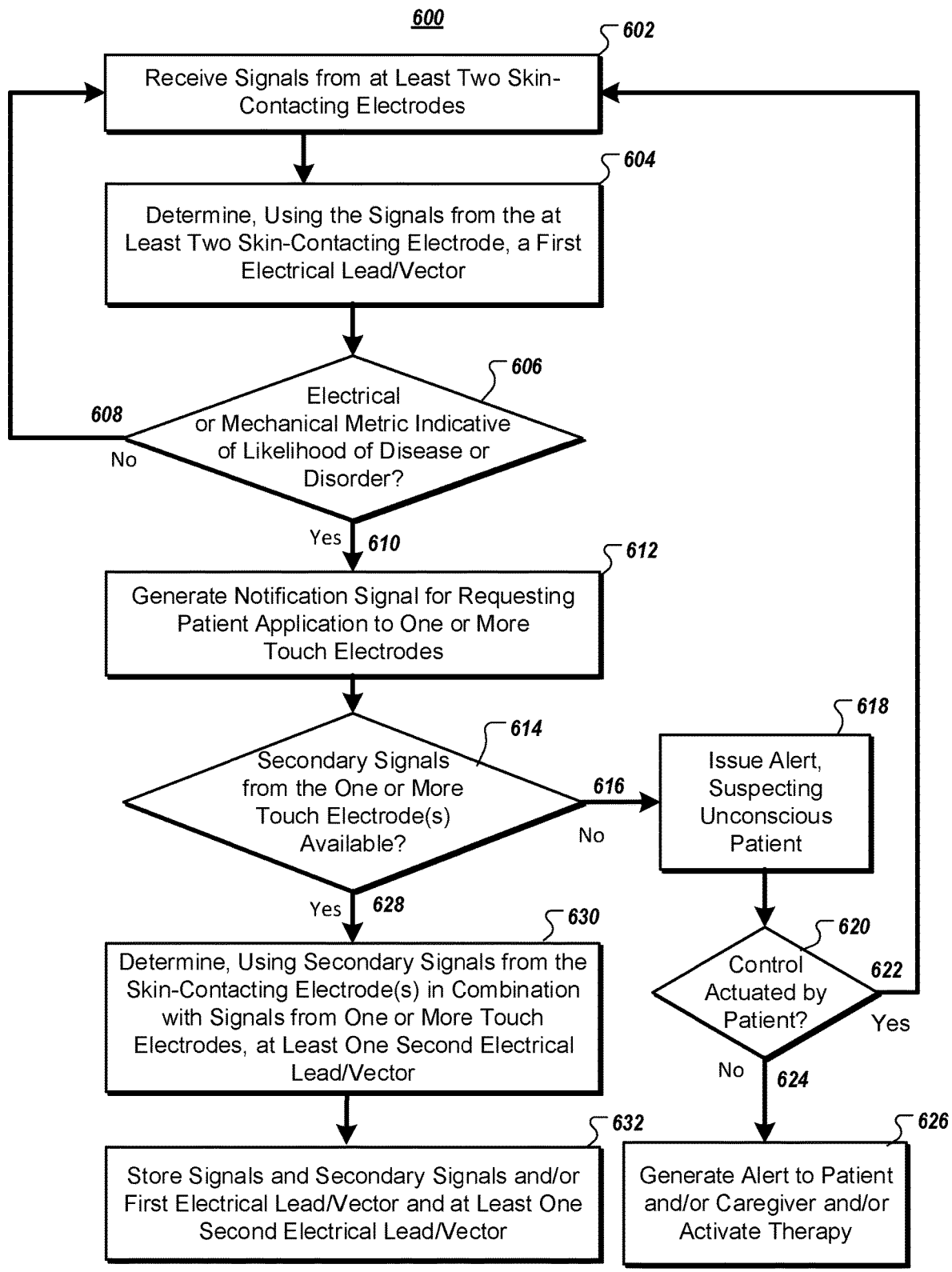
FIG. 6 is a flow chart of an example process for monitoring functioning of a patient's heart using a wearable medical device.

FIG. 6 is a flow chart of an example process 600 for monitoring functioning of a patient's heart using a wearable medical device such as the wearable medical device 200 of FIGS. 2A-F, the wearable medical device 300 of FIGS. 3A-C, or the wearable medical device 500 of FIG. 5. In some examples, the process 600 includes a number of steps that can be performed by one or more components of the medical device 200, 300, 500 including a computing device or system in communication with the medical device 200, 300, 500, such as a remote (e.g., cloud-based) computing system or portable computing device. In illustrative examples, the steps of the process 600 may be performed, in combination, by the medical device 200 and a remote computing system, or by the central controller 308 of FIG. 3B and a separate computing system or device.

In some implementation, the process 600 begins with receiving signals from at least two skin-contacting electrodes (602). For example, the at least two skin-contacting electrodes can be the at least two skin-facing electrodes 220a-b of FIG. 2A-2F, electrodes 320 of FIGS. 3A-3C, or electrodes 560a-e of FIG. 5. In an example, the at least one processor can be configured to receive signals from at least two skin-contacting electrodes. The step of receiving signals can include evaluating signal quality and identifying and reducing ECG signal corruption. In some implementation, the step of receiving signals can include receiving secondary touch signals from a second touch electrode (the patient applies a finger from each arm to a respective touch electrode), generating a second lead, and performing common-mode interference or QRST cancellation using the second lead formed from the secondary touch signals.

Referring to FIGS. 3A and 3B, if the second substrate 304 is positioned such that the skin-facing electrode 320 is aligned approximately with the standard LL (left-leg) ECG electrode position and is connected to a first input of a first ECG monitor circuit, and a first touch electrode is connected to a second input of the first ECG monitor circuit then, when the patient contacts the first touch electrode 330, the generated vector can be the standard ECG Lead III vector. If, in addition, the skin-facing electrode 320 in the LL ECG electrode position is connected to the first input of a second ECG monitor circuit, and the second touch electrode 332 is available and is connected to the second input of the second ECG monitor circuit, then a second generated vector is the standard ECG Lead II vector. If the first touch electrode 330 is connected to the first input of a third ECG monitor circuit and the second touch electrode 332 is connected to the second input of the third ECG monitor circuit, then a third generated vector is the standard ECG Lead I.

In some implementations, the signals from at least two skin-contacting electrodes are used to determine a first electrical lead/vector (604). In an example, determining the first electrical lead/vector can include identifying ECG signal frequencies by performing a Fast Fourier Transform. In some embodiments, determining the first electrical lead/vector includes identifying a baseline morphology template based on heart rate and morphology. Examples of baseline morphology templates include identifying ECG signatures (e.g., P-wave, a QRS complex, non-standard vectors), heart vibrations, and a cardiac condition (e.g., ventricular arrhythmia).

In some implementations, it is determined whether an electrical and/or mechanical metric is indicative of likelihood of disease or disorder (606). In an example, the determination if the electrical and/or mechanical metric is indicative of likelihood of disease or disorder, can be based on a comparison of the patient's current cardiac data/morphology template (e.g., QRS complex) to their baseline morphology template. When the determination is that the metric is not indicative of likelihood of disease or disorder (608), in some implementations, the process 600 returns to receiving signals (602). When the determination is that the metric is indicative of likelihood of disease or disorder (610), in some implementations, a notification signal for requesting patient application to one or more touch electrodes is generated (612). In an example, the determination that the metric is indicative of likelihood of disease or disorder can be when the baseline morphology template and the current morphology template do not substantially match. (See FIGS. 1F-G). In an example, notifying can include initiating an output device (e.g., vibration element, speaker, alarm, light) to output a notification to the patient to apply their finger or portion of their arm to one or more of touch electrodes.

In an example, rather than determining a likelihood of disease or disorder and/or requesting the patient to touch the one or more touch electrodes (steps 606 and 612), process 600 may instead detect when secondary signals from the one or more touch electrodes are available. In such an implementation, as noted above, the patient may proactively place a finger or other portion of the patient's arm on the one or more touch electrodes. The patient's actions in this regard, can initiate the monitoring of the secondary signals.

In some implementations, it is determined when secondary signals from the one or more touch electrodes are available (614). For example, the one or more processors may review incoming data for a signature of a touch electrode. In another example, signal processing may determine whether a consistent, usable signal is being obtained via at least one touch electrode (e.g., whether the patient is maintaining adequate contact). When the determination is that the secondary signals from the one or more touch electrodes is not available (616), in some implementations, an alert is issued, responsive to suspecting the patient is unconscious (618). Further, it may be determined whether a control has been actuated by the patient (620). In some examples, to acknowledge the signal and alert the process 600 to patient responsiveness, the patient may press and hold one or more response buttons, issue a verbal command, or begin to maintain contact with the touch electrode(s). If the control is actuated by the patient (622), in some implementations, the process 600 returns to receiving signals (602). For example, the touch electrode(s) may be malfunctioning or may be inaccessible to the patient (e.g., due to present positioning or present wardrobe), such that the process 600 is unable to obtain the additional signals from the touch sensor at this time. Alternatively, if the control actuation involves touching the touch electrode, the process may instead move to processing signals obtained via the touch electrode(s) (620).

In some implementations, if the control has not been actuated by the patient (624), an escalating alert may be generated for attention of the patient and/or caregiver. For example, the patient and/or a caregiver may be alerted to the patient's non-responsiveness via a verbal message or shrill alarm produced by the medical device. In another example, a caregiver may be remotely alerted regarding a potential medical problem via a text message, smart phone application, or other computing device interface. Alternatively or additionally, in some implementations, therapy is activated (626). For example, as described in relation to medical device 500 of FIG. 5, a defibrillation process may be initiated. The therapy, in some embodiments, may be determined through analysis of available ECG signals. Alternatively or additionally, in some implementations, the escalating alert may direct the patient to wear a therapy-enabled device, for example, as described in relation to medical device 500 of FIG. 5 and the LifeVest® wearable cardioverter defibrillator available from ZOLL® Medical Corporation.

Returning to step 614, in some implementations, upon determining the secondary signals from the one or more touch electrodes are available (628) at least one second electrical lead/vector is determined using the secondary signals from the skin-contacting electrode(s) in combination with signals from one or more touch electrodes (630). A second electrical lead/vector is formed by detecting a secondary signal between one of the skin-contacting electrode(s) and one of the one or more touch electrodes. In some implementations, the secondary signal may not be sufficient to establish an appropriate ECG or cardiac signal. If a high impedance is detected, the medical device can activate the vibrating element to enhance contact with the skin of the patient. In an example, the electrical lead/vector displays uncharacteristic signatures for an expected electrical lead/vector. If the medical device expected a different portion of the patient's skin (e.g., left vs. right) a message can be delivered to instruct the patient to select a particular arm (e.g., left vs. right) for holding their skin to the touch electrode. If the medical device expected both a left and a right portion of the patient's skin (e.g., left and right arm) a message can be delivered to instruct the patient to place both arm for holding their skin to each touch electrode. If the medical device sensed that the patient is touching the same touch electrode with both a left and a right portion of the patient's skin, a message can be delivered to instruct the patient to place each arm on a separate touch electrode.

In some implementations, upon determining the at least one second electrical lead/vector, signals and secondary signals and/or the first electrical lead/vector and at least one second electrical lead/vector are stored for further processing (632). The storing of step 632 can be done locally on the memory of the medical device, as well as remotely, on a remote server. For example, the data may be stored locally on a memory, then uploaded in bulk transfers to a remote server for analysis.

Although illustrated in a particular series of steps, in other embodiments, more or fewer steps may be included in the process 600. For example, in further embodiments, the process 600 may include analyzing additional metrics or data, such as signals supplied by the transducer 250 of FIGS. 2B-2F. The additional metrics or data, for example, may inform whether to escalate the alert (626) to activating therapy (e.g., whether heart rate, respiration, or other metrics are indicative of an emergency situation). In still other implementations, one or more of the steps of the process 600 may be performed in a different order, or steps may be performed in parallel. For example, although illustrated as completing at step 632, in reality the process 600 would continue with receiving signals from the skin-contacting electrodes (602), which is a continuous monitoring process running in parallel with other steps of the process 600. Determining the first electrical lead or vector (604), for example, may include storing and transmitting for analysis, as described in relation to step 632. Additionally, if signals from the touch electrode(s) continue to be available, the process 600 may continue to analyze these signals as well (632).

Figure 7A:
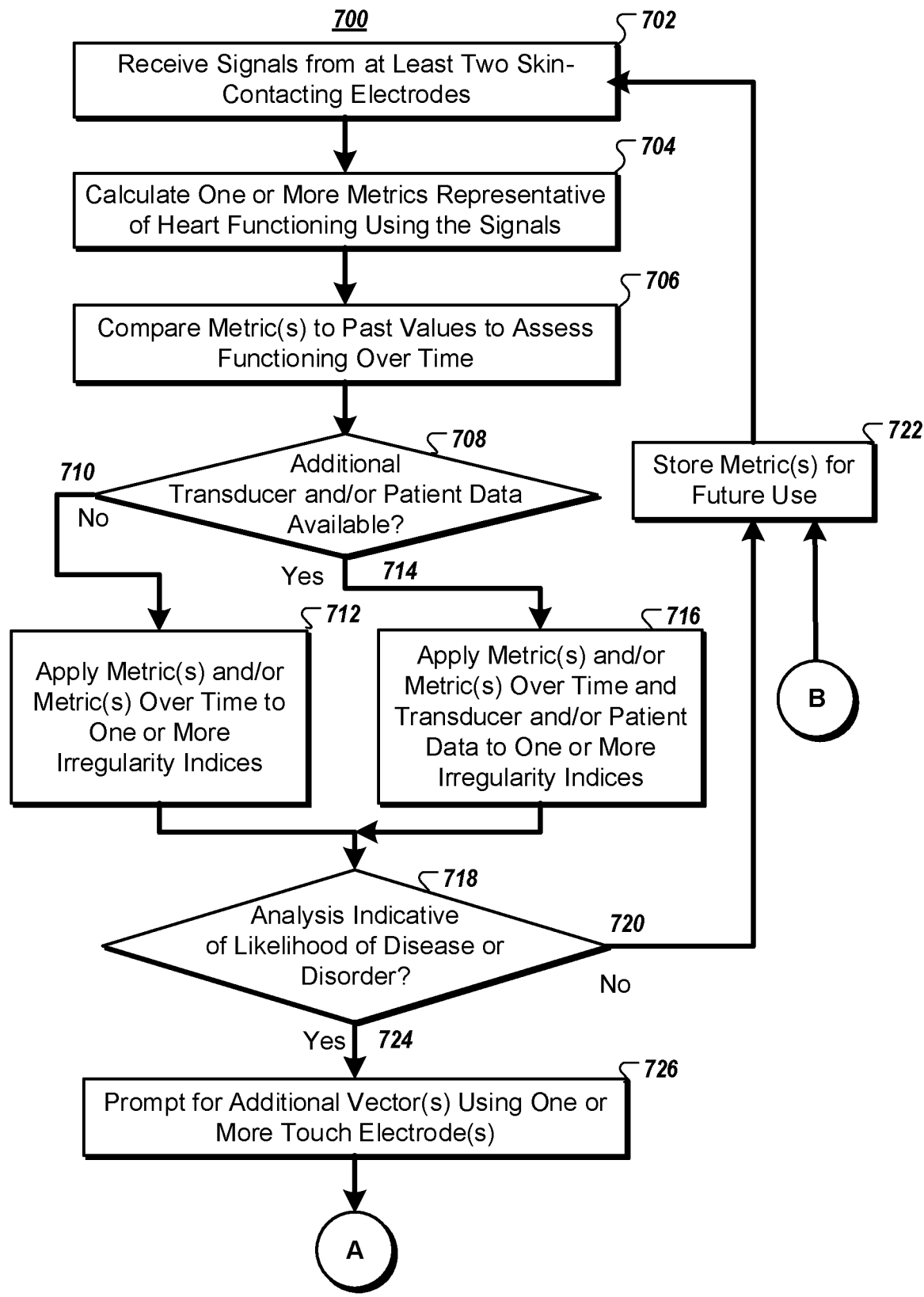
FIGS. 7A and 7B are a flow chart of an example process for analyzing signals obtained from electrodes of a wearable medical device such as those described in relation to FIGS. 2A through 5.
Figure 7B:
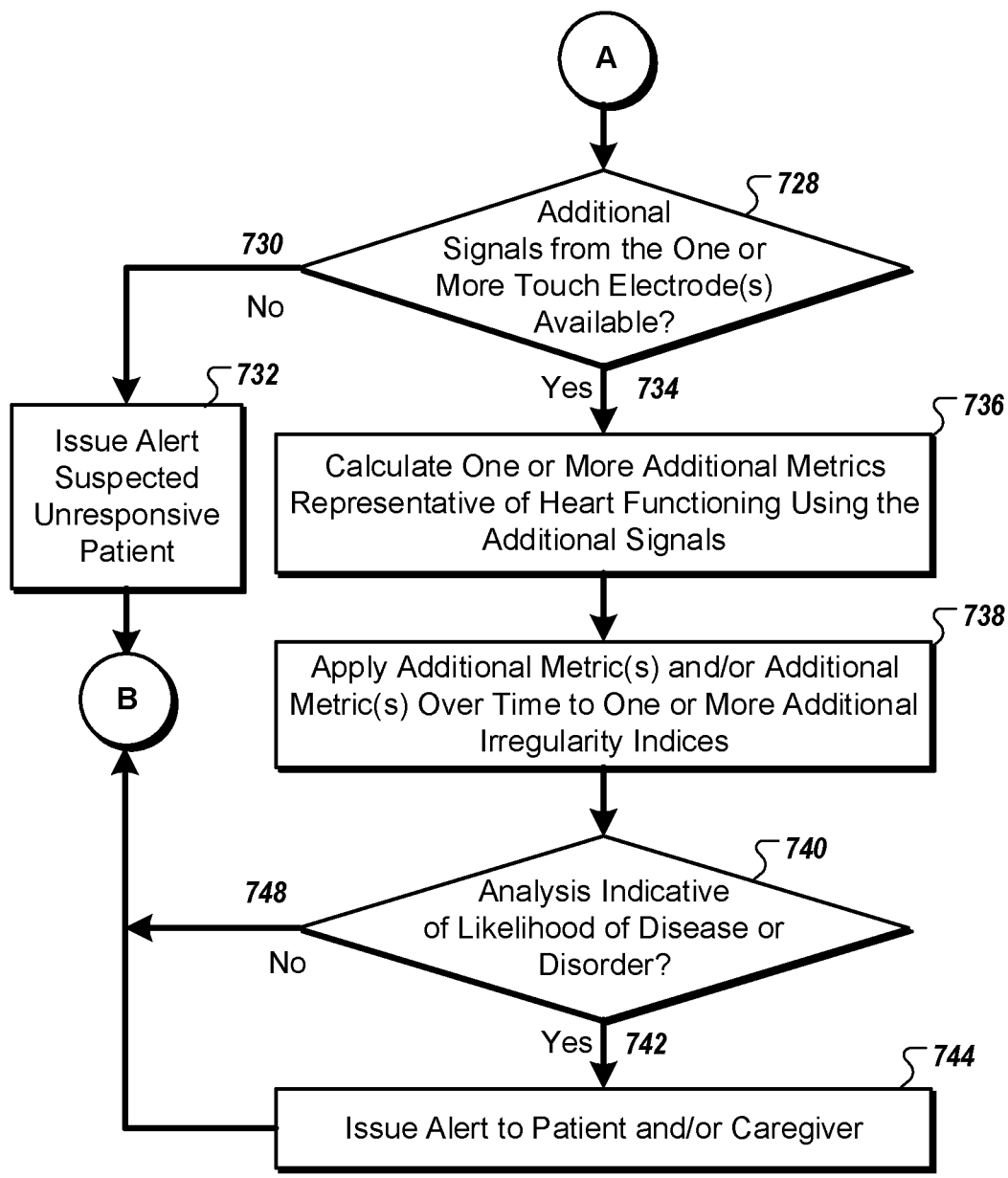

FIGS. 7A and 7B are a flow chart of an example process 700 for analyzing signals obtained from electrodes of a wearable medical device such as the wearable medical device 200 of FIGS. 2A-F, the wearable medical device 300 of FIGS. 3A-C, or the wearable medical device 500 of FIG. 5. In some examples, the process 700 includes a number of steps that can be performed by one or more components of the medical device 200, 300, 500 including a computing device or system in communication with the medical device 200, 300, 500, such as a remote (e.g., cloud-based) computing system or portable computing device. In illustrative examples, the steps of the process 700 may be performed, in combination, by the medical device 200 and a remote computing system, or by the central controller 308 of FIG. 3B and a separate computing system or device.

In some implementations, the process 700 begins with receiving signals from at least two skin-contacting electrodes (702). For example, the at least two skin-contacting electrodes can be the at least two skin-facing electrodes 220*a-b* of FIG. 2A-2F, electrodes 320 of FIGS. 3A-3C, or electrodes 560*a-e* of FIG. 5.

In some implementations, one or more metrics representative of heart functioning are calculated using the signals (704). The metrics, in some embodiments, include the patient's ECG cardiac data/morphology template (e.g., QRS complex). The metrics may be calculated, for example, using vectorcardiographic analysis techniques for analyzing loop parameters like shape, angle, and areal. Vector loop analysis via shape or other means can help to distinguish between healthy ECG rhythms and life-threatening arrhythmias such as VT or ventricular fibrillation (VF), or in detecting elevated risk of a medical event occurring at some time in the future. Vector loop analysis is described further in U.S. Pat. No. 9,545,209B2, "VCG Vector Loop Bifurcation", and U.S. Patent application US20160135706A1, "Medical Premonitory Event Estimation", which are each incorporated by reference in its entirety. In some implementations, the two ECG electrodes 220*a-b* have prefixed spacing to form a precordial lead. Re-positional electrodes 320 can form any standard or non-standard lead.

In some implementations, the one or more metrics representative of heart functioning are compared to past values to assess functioning over time (706). For example, a patient baseline may be stored in local or remote storage for use in comparing changes over time. In another example, a subsequent time period may be compared to the prior time period to monitor changes in heart functioning in near-real-time.

In some implementations, it is determined whether additional transducer and/or patient data is available (708). The additional data, in some examples, may be supplied by the transducer 250 of FIGS. 2B-2F, a separate patient biometrics monitoring device, or other sensors of the medical device. In some embodiments, the additional patient data includes demographics, disease, medication, or other personal data stored locally or in a remote computing system.

When additional transducer and/or patient data is not available (710), metric(s) and/or metric(s) over time can be applied to one or more irregularity indices (712). The irregularity indices, for example, can include a change in ECG signal pattern frequency (e.g., FFT), power, amplitude, phase, and rate of change, RR variability, low heart rate (under 40), escalated heart rate (over 140).

When additional transducer and/or patient data is available (714), metric(s) and/or metric(s) over time and transducer and/or patient data can be applied to one or more irregularity indices (716). The irregularity indices, for example, can include a change in an amount of fluid in the patient's lungs and chest cavity, a respiration rate that is ramping up/down or above/below a respiration threshold (e.g., over 15 breaths/min, under 8 breaths/min), abnormal vibrations of the patient (e.g., S3 more pronounced over time, distance between r-wave peak and valve closure). In this circumstance, in some embodiments, a more patient-specific or circumstance-specific irregularity index may be applied to determine whether the present heart functioning metrics are indicative of a problem condition. In other embodiments, the additional data may be considered in weighting the results of analyzing the metrics in light of the irregularity indices. For example, rather than a binary "good" or "bad", there may be a range of outcomes of the analysis against the irregularity indices. In this case, if the results fall not within a "clear problem" range but instead in a "potential problem" range, the additional patient data or transducer metrics may be applied to make a determination of whether there is a cause for alarm.

In some implementations, if the outcome of the analysis at step 712 or 716 is not determined (718) to be indicative of likelihood of disease or disorder (720), the metrics are stored for future use (722). For example, the outcome may be stored for comparison at step 706. Further, the metrics may be uploaded to a remote computing system for historic analysis and future review by a medical professional. At this point, in some implementations, the process 700 returns to receiving signals from the at least two skin-contacting electrodes (702).

If, instead, the analysis is indicative of likelihood of disease or disorder (724), in some implementations, the patient is prompted to provide information for additional vector(s) using one or more touch electrode(s) (726). For example, the controller, upon detection of a threshold difference between monitored data and acceptable health metrics may trigger prompting of the patient. The prompting, for example, can be provided by the controller (e.g., through verbal instruction to the patient). In another example, the prompting may be supplied through a portable computing device application such as a smart phone app designed to supply prompts to the user to obtain data. In another example, the prompts may be supplied to the user upon detection of an irregularity in continuously monitored patient data, such as ECG data, respiratory data, heart rate data, or other bioinformation.

Turning to FIG. 7B, in some implementations, monitoring begins to identify signals from the one or more touch electrodes (728). For example, the patient may be provided a period of time to move any articles of clothing out of the way, get to a comfortable position, and begin maintaining a portion of an arm upon a touch electrode. The patient, in one example, may set one or more fingertips on the touch electrodes. In another example, a portion of a palm or a wrist may be held against the touch electrode. Further, in some embodiments, a first may be held against an electrode such that a side of a hand is maintained against the touch electrode. When additional signals from the one or more touch electrode(s) are not available (730), in some implementations, an alert may be issued (732). For example, the alert may be issued due to anticipating that the patient may be unresponsive and in need of help. In another example, the patient may be asleep and requiring a louder or otherwise more insistent alarm to comply with the request for additional information. In some implementations, the current metrics are once again stored for future use (722). Additional description regarding potential handling of an unresponsive patient are provided in steps 620 and 626 of FIG. 6.

In some implementations, when additional signals from the one or more touch electrode(s) are available (734), one or more additional metrics representative of heart functioning are calculated using the additional signals (736). For example, the additional metrics can include ECG signals derived from a larger vector, a lead/vector separated by at least 15° from a corresponding first one or more ECG leads, enhanced detection of atrial depolarization of the heart (better P-wave detection), enhanced detection of R-wave characteristics, lower signal artifacts, and better heart rate detection characteristics relative to the first one or more ECG leads.

In some implementations, the additional metric(s) and/or additional metric(s) over time are applied to one or more additional irregularity indices (738). For example, as the patient continues to maintain contact with at least one touch electrode, analysis of subsequent time periods may be compared to analysis of prior time periods to monitor any changes in metrics over time. Further, baseline data, obtained previously (e.g., upon device setup, on a prior day, 6 hours ago, etc.) may be used as a comparison metric to determine changes in metrics obtained through the touch electrode(s). Different irregularity indices, in some embodiments, are applied to metrics obtained via the touch electrode(s). For example, P-wave analysis may be possible only using the touch electrodes. For example, the skin-facing electrodes 220 of the medical device 200 of FIGS. 2A-F may be positioned too close together for dependable P-wave analysis.

In some implementations, based upon the analysis of the additional metrics, it is determined whether there is likelihood of disease or disorder (740). As with step 718, additional transducer or patient data may also be applied to this analysis.

In some implementations, when the analysis is indicative of likelihood of disease or disorder (742), an alert is issued to the patient and/or caregiver (744). For example, the patient and/or a caregiver may be alerted to the patient's non-responsiveness via a verbal message or shrill alarm produced by the medical device. In another example, a caregiver may be remotely alerted regarding a potential medical problem via a text message, smart phone application, or other computing device interface.

Whether or not it is determined that the analysis is indicative of likelihood of disease or disorder (742, 748), in some implementations, the additional metric(s) are stored for future use (722).

Although illustrated in a particular series of steps, in other embodiments, more or fewer steps may be included in the process 700. For example, in further embodiments, the process 700 may include streaming raw sensor data directly. In some implementations, monitoring can originate (702) or continue (728) identifying signals from the transducer 250 of FIGS. 2B-2F, where metrics and signals supplied by the transducer 250. In still other implementations, one or more of the steps of the process 700 may be performed in a different order, or steps may be performed in parallel. Calculating one or more metrics representative of heart functioning (704), for example, may include issuing an alert to the patient and/or caregiver as described in relation to step 744. Additionally, if signals from the additional transducer and/or patient data is determined to be indicative of likelihood of disease or disorder (718), the process 700 may continue to directly issue an alert to the patient and/or caregiver as described in relation to step 744.

Example Controller

Figure 8:
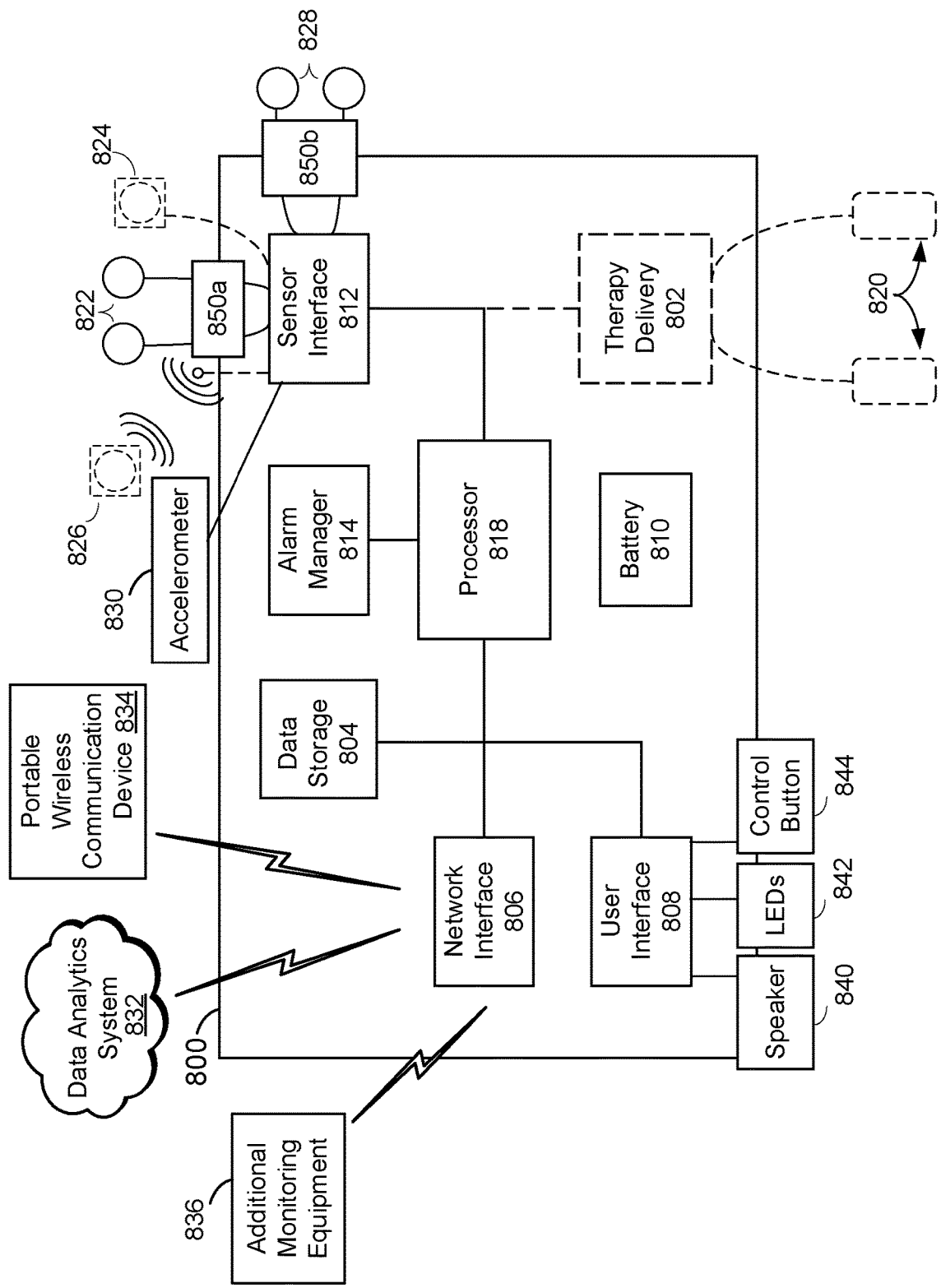
FIG. 8 is a block diagram of an example system for obtaining heart functionality metrics using a wearable medical device such as those described in relation to FIGS. 2A through 5.

FIG. 8 illustrates a sample component-level view of a medical device controller, such as the medical device controller 308 of FIG. 3B, the medical device controller 520 of FIG. 5, or controller processing circuitry built into the substrate of the medical device 300 of FIGS. 2A-F or the medical device 300 of FIGS. 3A and 3C. As shown in FIG. 8, the medical device controller 800 can include a therapy delivery circuit 802, a data storage 804, a network interface 806, a user interface 808, at least one battery 810, a sensor interface 812, an alarm manager 814, and at least one processor 818. Further, a patient monitoring medical device, such as the medical device 200 of FIGS. 2A-2F or the medical device 300 of FIGS. 3A-3C, can include the medical device controller 800 that includes like components as those described above, but does not include the therapy delivery circuit 802 (shown in dotted lines).

The therapy delivery circuit 802 can be coupled to one or more electrodes 820 configured to provide therapy to the patient (e.g., therapy electrodes 514 as described above in connection with FIG. 5). For example, the therapy delivery circuit 802 can include, or be operably connected to, circuitry components that are configured to generate and provide the therapeutic shock. The circuitry components can include, for example, resistors, capacitors, relays and/or switches, electrical bridges such as an h-bridge (e.g., including multiple insulated gate bipolar transistors or IGBTs), voltage and/or current measuring components, and other similar circuitry components arranged and connected such that the circuitry components work in concert with the therapy delivery circuit and under control of the at least one processor (e.g., processor 818) to provide, for example, one or more pacing or defibrillation therapeutic pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank having multiple capacitors (e.g., two, three, four or more capacitors). These capacitors can be switched into a series connection during discharge for a defibrillation pulse. For example, four capacitors of approximately 650 uF can be used. The capacitors can have between 350 to 500 volt surge rating and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuit 802 can be configured to perform the switching and pulse delivery operations, e.g., under control of the at least one processor 818. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 804 can include one or more of non-transitory computer readable media, such as flash memory, solid state memory, magnetic memory, optical memory, cache memory, combinations thereof, and others. The data storage 804 can be configured to store executable instructions and data used for operation of the medical device controller 800. In certain implementations, the data storage can include executable instructions that, when executed, are configured to cause the at least one processor 818 to perform one or more functions, such as portions of the process 600 of FIG. 6 or portions of the process 700 of FIGS. 7A and 7B.

In some examples, the network interface 806 can facilitate the communication of information between the medical device controller 800 and one or more other devices or entities over a communications network. For example, where the medical device controller 800 is included in an ambulatory medical device (such as medical device 200 of FIGS. 2A-F, medical device 300 of FIGS. 3A-3C, or medical device 500 of FIG. 5), the network interface 806 can be configured to communicate with a remote data analytics system 832 such as a remote server, cloud computing environment, or other similar computing device. The remote data analytics system 832, for example, may be used to perform analysis and historic comparison of data derived through the sensor interface 812.

The network interface 806, in some implementations, can facilitate communication between the medical device controller 800 and a portable wireless communication device 834. In some embodiments, rather than directly communicating with the data analytics system 832, the portable wireless communication device 834 may provide a network conduit, for example receiving data from the medical device controller 800 via a short-range communication link such as a Bluetooth or RF communication interface provided by the network interface 806. The portable wireless communication device 834 may then perform some local analysis of the data and/or communicate the data to the data analytics system 832. Further, in some embodiments, the portable wireless communication device 834 may provide user interface capabilities beyond the capabilities of the user interface 808. For example, while the medical device may be directly attached to the patient and therefore not readily observed for receiving information such as text messages or lighted displays, an enhanced patient interface may be presented to the patient through coordinating communications with the portable wireless communication device 834.

In some implementations, the network interface 806 is configured to communicate with additional monitoring equipment 836, such as, in some examples, a pulse monitoring device, sleep apnea monitoring device, respiratory monitoring device, or other biometric collection device. This additional patient data may be used by the processor and/or the data analytics system 832 to fine-tune analysis.

In certain implementations, the user interface 808 can include one or more physical interface devices such as input devices, output devices, and combination input/output devices and a software stack configured to drive operation of the devices. These user interface elements may render visual, audio, and/or tactile content. Thus, the user interface 808 may receive input or provide output, thereby enabling a user to interact with the medical device controller 800. In particular examples, the user interface 808 may include a speaker element 840 and light emitting diodes (LEDs) 842. Further, in some implementations, the user interface 808 includes a control button 844 for providing settings communication and/or for supplying a response upon the alarm manager 814 triggering an alert regarding an unresponsive patient. The control button 844, for example, may override functionality by indicating that the patient is not unconscious.

The medical device controller 800 can also include at least one battery 810 configured to provide power to one or more components integrated in the medical device controller 800. The battery 810 can include a rechargeable multi-cell battery pack. In one example implementation, the battery 810 can include three or more 2200 mAh lithium ion cells that provide electrical power to the other device components within the medical device controller 800. For example, the battery 810 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 800.

The sensor interface 812 can be coupled to one or more sensors configured to monitor one or more physiological parameters of the patient. As shown, the sensors may be coupled to the medical device controller 800 via a wired or wireless connection. The sensors can include one or more electrocardiogram (ECG) electrodes 822 (e.g., similar to skin-facing electrodes 220 of FIGS. 2A-2F, skin-facing electrodes 320 of FIGS. 3A-3C, or sensing electrodes 512 of FIG. 5), heart vibrations sensors 824 (e.g., similar to transducer 250 of FIGS. 2B-2F), and tissue fluid monitors 826 (e.g., based on ultra-wide band radiofrequency devices, possibly provided by transducer 250 of FIGS. 2B-2F). Further, the sensors can include one or more intermittently-activated touch sensors 828, such as the touch sensors 230 of FIGS. 2A-2F, the touch sensors 330 of FIGS. 3A-3C, or the touch sensors 560 of FIG. 5. The touch sensors, similar to the ECG sensors, may include ECG electrodes. Further, the touch sensors 230 may include proximity sensors, vibrating feedback elements, or pressure sensors to identify and/or encourage user interaction with the touch sensors 230.

The ECG electrodes 822 can monitor a patient's ECG information. For example, the ECG electrodes 822 can be conductive electrodes, e.g., a metallic element disposed on a substrate and in some cases, includes an electrolytic gel to facilitate ECG detection. As an example, such conductive ECG electrodes are comprised of a plastic substrate covered with a silver/silver chloride ionic compound. Silver chloride is only very slightly soluble in water, so it can remain relatively stable. The conductive electrode can be assembled with an electrolyte gel in which a principle anion is Cl–. Cl– is an attractive anion for electrode applications because the skin interface contains an excess of chloride ions in solution (e.g., perspiration).

In some implementations, the ECG electrodes 822 can be dry electrodes, e.g., a metallic element substrate with an oxide coating disposed on a substrate. Dry electrodes comprise metal electrodes with oxide coatings such as tantalum pentoxide electrodes, as described in, for example, U.S. Pat. No. 6,253,099 entitled "Cardiac Monitoring Electrode Apparatus and Method," the content of which is incorporated herein by reference.

The ECG electrodes 822 are configured to measure changes in a patient's electrophysiology by measuring the patient's ECG information. ECG circuitry 850a associated with the ECG electrodes 822 can transmit information descriptive of the ECG signals to the sensor interface 812 for subsequent analysis. Likewise, ECG circuitry 850b associated with the one or more intermittently-activated touch sensors 828 can transmit information descriptive of the ECG signals to the sensor interface 812 for subsequent analysis.

The heart vibrations sensors 824 can detect a patient's heart vibration information. For example, the heart vibrations sensors 824 can be configured to detect heart vibration values including any one or all of S1, S2, S3, and S4. From these heart vibration values, certain heart vibration metrics may be calculated, including any one or more of EMAT, % EMAT, SDI, and LVST. The heart vibrations sensors 824 can include an acoustic sensor configured to detect vibrations from a subject's cardiac system and provide an output signal responsive to the detected heart vibrations. The heart vibrations sensors 824 can also include a multi-channel accelerometer 830, for example, a three channel accelerometer configured to sense movement in each of three orthogonal axes such that patient movement/body position can be detected and correlated to detected heart vibrations information. The heart vibrations sensors 824 can transmit information descriptive of the heart vibrations information to the sensor interface 812 for subsequent analysis.

The tissue fluid monitors 826 can use RF based techniques to assess fluid levels and accumulation in a patient's body tissue. For example, the tissue fluid monitors 826 can be configured to measure fluid content in the lungs, typically for diagnosis and follow-up of pulmonary edema or lung congestion in heart failure patients. The tissue fluid monitors 826 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 826 can transmit information descriptive of the tissue fluid levels to the sensor interface 812 for subsequent analysis.

The sensor interface 812 can be coupled to any one or combination of sensing electrodes/other sensors to receive other patient data indicative of patient parameters via the ECG circuitry 850a-b. Once data from the sensors has been received by the sensor interface 812, the data can be directed by the at least one processor 818 to an appropriate component within the medical device controller 800. For example, if heart data is collected by heart vibrations sensor 824 and transmitted to the sensor interface 812, the sensor interface 812 can transmit the data to the at least one processor 818 which, in turn, relays the data to a cardiac event detector. The cardiac event detector, for example, may perform a portion of the steps of process 600 of FIG. 6 or of process 700 of FIGS. 7A and 7B. The cardiac event data can also be stored on the data storage 804.

In certain implementations, the alarm manager 814 can be configured to manage alarm profiles and notify one or more intended recipients of events specified within the alarm profiles as being of interest to the intended recipients. These intended recipients can include external entities such as users (patients, physicians, and monitoring personnel) as well as computer systems (monitoring systems or emergency response systems). The alarm manager 814 can be implemented using hardware or a combination of hardware and software. For instance, in some examples, the alarm manager 814 can be implemented as a software component that is stored within the data storage 804 and executed by the at least one processor 818. In this example, the instructions included in the alarm manager 814 can cause the at least one processor 818 to configure alarm profiles and notify intended recipients using the alarm profiles. In other examples, alarm manager 814 can be an application-specific integrated circuit (ASIC) that is coupled to the at least one processor 818 and configured to manage alarm profiles and notify intended recipients using alarms specified within the alarm profiles. Thus, examples of alarm manager 814 are not limited to a particular hardware or software implementation.

In some implementations, the at least one processor 818 includes one or more processors (or one or more processor cores) that each are configured to perform a series of instructions that result in manipulated data and/or control the operation of the other components of the medical device controller 800. In some implementations, when executing a specific process (e.g., cardiac monitoring), the at least one processor 818 can be configured to make specific logic-based determinations based on input data received, and be further configured to provide one or more outputs that can be used to control or otherwise inform subsequent processing to be carried out by the at least one processor 818 and/or other processors or circuitry with which processor 818 is communicatively coupled. Thus, the at least one processor 818 reacts to specific input stimulus in a specific way and generates a corresponding output based on that input stimulus. In some example cases, the at least one processor 818 can proceed through a sequence of logical transitions in which various internal register states and/or other bit cell states internal or external to the at least one processor 818 may be set to logic high or logic low. As referred to herein, the at least one processor 818 can be configured to execute a function where software is stored in a data store coupled to the at least one processor 818, the software being configured to cause the at least one processor 818 to proceed through a sequence of various logic decisions that result in the function being executed. The various components that are described herein as being executable by the at least one processor 818 can be implemented in various forms of specialized hardware, software, or a combination thereof. For example, the at least one processor can be a digital signal processor (DSP) such as a 24-bit DSP processor. The at least one processor can be a multi-core processor, e.g., having two or more processing cores. The at least one processor can be an Advanced RISC Machine (ARM) processor such as a 32-bit ARM processor. The at least one processor can execute an embedded operating system, and include services provided by the operating system that can be used for file system manipulation, display & audio generation, basic networking, firewalling, data encryption and communications.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A wearable cardiac monitor for continuously monitoring one or more cardiac physiological parameters of a patient, the wearable cardiac monitor comprising:
   an adhesive patch configured for application to a torso of the patient, the adhesive patch comprising
      a skin-facing surface including
         two or more first ECG electrodes positioned for continuous contact with skin of the torso of the patient, and
         at least one adhesive region configured to maintain the adhesive patch against the skin of the torso, and
      an external surface including a touch ECG electrode configured to be accessible for touching by the patient;
   at least one ECG monitor circuit in communication with the two or more first ECG electrodes and the touch ECG electrode, the at least one ECG monitor circuit being configured to
      continuously calculate at least one first electrical lead, each lead of the at least one first electrical lead being formed based on ECG signals collected by at least two electrodes of the two or more first ECG electrodes, and
      upon signal availability due to the patient touching the touch ECG electrode, calculate at least one second electrical lead being formed based on ECG signals collected by at least one of the two or more first ECG electrodes and the touch ECG electrode; and
   processing circuitry configured to
      continuously analyze the at least one first electrical lead to identify the one or more cardiac physiological parameters of the patient, and
      responsive to availability of the at least one second electrical lead, analyze the at least one second electrical lead in view of the at least one first electrical lead.

2. The wearable cardiac monitor of claim 1, wherein the processing circuitry is configured to, prior to the analyzing the at least one second electrical lead, identify contact with the touch ECG electrode by the patient.

3. The wearable cardiac monitor of claim 1, wherein the processing circuitry is further configured to identify, based on the analyzing the at least one second electrical lead in view of the at least one first electrical lead, whether an abnormal physiological function is present.

4. The wearable cardiac monitor of claim 3, wherein the abnormal physiological function comprises one or more of fibrillation, bradycardia, tachycardia, atria-ventricular block, Lown-Ganong-Levine syndrome, atrial flutter, sino-atrial node dysfunction, cerebral ischemia, syncope, atrial pause, or heart palpitations.

5. The wearable cardiac monitor of claim 1, further comprising a network interface, wherein at least a portion of the processing circuitry is in communication with the adhesive patch via the network interface.

6. The wearable cardiac monitor of claim 1, wherein the processing circuitry is further configured to issue a message to the patient regarding touching the touch ECG electrode.

7. The wearable cardiac monitor of claim 6, wherein the message is issued responsive to recognizing, via the analyzing the at least one first electrical lead, one or more aberrant patterns indicative of an abnormal physiological function.

8. The wearable cardiac monitor of claim 1, wherein the wearable cardiac monitor is configured to monitor for at least a week, at least one month, or over several months.

9. The wearable cardiac monitor of claim 1, further comprising another touch ECG electrode configured to be accessible for touching by the patient.

10. The wearable cardiac monitor of claim 9, wherein:
the touch ECG electrode is configured for touching by a portion of a right hand of the patient; and
the another touch ECG electrode is configured for touching by a portion of a left hand of the patient.

11. The wearable cardiac monitor of claim 1, wherein the wearable cardiac monitor is configured to buffer at least a threshold time period of ECG data collected by the touch ECG electrode prior to the analyzing.

12. The wearable cardiac monitor of claim 1, wherein the external surface comprises at least one indentation for touch alignment.

13. The wearable cardiac monitor of claim 1, further comprising at least one acoustic transducer for detecting heart vibration signals.

14. The wearable cardiac monitor of claim 1, wherein the processing circuitry is further configured to, responsive to identifying an abnormal physiological function is present, generate an alert.

15. A system for continuously monitoring one or more cardiac physiological parameters of a patient, the system comprising:
an adhesive patch configured for application to a torso of the patient, the adhesive patch comprising
a skin-facing surface including
two or more first ECG electrodes positioned for continuous contact with skin of the torso of the patient, and
at least one adhesive region configured to maintain the adhesive patch against the skin of the torso, and
an external surface including a touch ECG electrode configured to be accessible for touching by the patient;
at least one ECG monitor circuit in communication with the two or more first ECG electrodes and the touch ECG electrode, the at least one ECG monitor circuit being configured to
calculate at least one first electrical lead, each lead of the at least one first electrical lead formed between signals collected by each electrode of a respective set of electrodes of the two or more first ECG electrodes, and
upon signal availability due to the patient touching the touch ECG electrode, calculate at least one second electrical lead formed between signals collected by one of the two or more first ECG electrodes and the touch ECG electrode;
a network interface configured to communicate with a remote server; and
a remote computing system configured to communicate with the network interface via the remote server, the remote computing system configured to
analyze the at least one first electrical lead to recognize one or more aberrant patterns indicative of an abnormal physiological function of a heart of the patient,
upon recognizing at least one of the one or more aberrant patterns, issue a command to the adhesive patch to prompt the patient to contact the touch ECG electrode, and
responsive to availability of the at least one second electrical lead, analyze the at least one second electrical lead in view of the at least one first electrical lead to confirm, based on the analyzing the at least one second electrical lead in view of the at least one first electrical lead, whether at least one abnormal physiological function is present.

16. The system of claim 15, wherein the network interface is configured to communicate with the remote server via a portable wireless communication device.

17. The system of claim 15, wherein the remote computing system is further configured to, responsive to confirming the at least one abnormal physiological function is present, generate an alert for attention of the patient and/or a caregiver.

18. The system of claim 17, wherein generating the alert comprises issuing a message to a remote device of the caregiver.

19. The system of claim 15, wherein, responsive to the remote computing system issuing the command to the adhesive patch to prompt the patient to contact the touch ECG electrode, a controller of the adhesive patch is configured to issue an audible alert or an audible message.

20. The system of claim 15, wherein confirming whether the at least one abnormal physiological function is present comprises comparing current cardiac data derived from the at least one first electrical lead and the at least one second electrical lead to historic patient cardiac data.

* * * * *